United States Patent
Hyde et al.

(10) Patent No.: US 9,682,245 B2
(45) Date of Patent: Jun. 20, 2017

(54) IMPLANTABLE HEART TREATMENT SYSTEMS, DEVICES, AND METHODS

(71) Applicant: Elwha LLC, Bellevue, WA (US)

(72) Inventors: Roderick A. Hyde, Redmond, WA (US); Edward K. Y. Jung, Bellevue, WA (US); Eric C. Leuthardt, St. Louis, MO (US); Gary L. McKnight, Bothell, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 42 days.

(21) Appl. No.: 14/676,090

(22) Filed: Apr. 1, 2015

(65) Prior Publication Data
US 2016/0287774 A1    Oct. 6, 2016

(51) Int. Cl.
*A61M 1/32* (2006.01)
*A61N 1/39* (2006.01)
(Continued)

(52) U.S. Cl.
CPC ......... *A61N 1/3962* (2013.01); *A61M 1/1678* (2013.01); *A61M 1/1698* (2013.01); *A61M 1/327* (2014.02); *A61N 1/362* (2013.01); *A61M 2202/0225* (2013.01); *A61M 2202/0233* (2013.01); *A61M 2202/0275* (2013.01);
(Continued)

(58) Field of Classification Search
CPC ............ A61M 2202/0476; A61M 1/32; A61M 2202/0225; A61M 2202/0233; A61M 2202/0275; A61M 2202/0283; A61M 2205/054; Y10T 137/87652; A61N 1/3987
See application file for complete search history.

(56) References Cited

U.S. PATENT DOCUMENTS

| 5,091,404 | A | 2/1992 | Elgebaly |
| 7,092,753 | B2 | 8/2006 | Darvish et al. |

(Continued)

OTHER PUBLICATIONS

Hung, Vuylsteke, and Valchanov, Extracorporeal Membrane Oxygenation: Coming to an ICU Near You, J. Intensive Care Society., vol. 13, 31-38 (2012).
(Continued)

*Primary Examiner* — Deborah Malamud
(74) *Attorney, Agent, or Firm* — Daniel J. Honz; Advent, LLP

(57) ABSTRACT

Treatment of cardiac tissue via an implantable heart treatment device is described. A device embodiment includes, but is not limited to, a substrate configured for implantation within a body; an electromagnetic signal generator coupled to the substrate and configured to generate one or more electric signals configured to stimulate one or more tissues of a heart; and an oxygenator coupled to the substrate and configured to supply one or more oxygenated molecules to one or more tissues of the heart, the oxygenator including a blood inlet portion, a blood outlet portion, and an oxygen exchange portion positioned between the blood inlet portion and the blood outlet portion, the oxygen exchange portion including a high surface area oxygen exchanger configured to transfer one or more oxygenated molecules from the high surface area oxygen exchanger to blood passing from the blood inlet portion to the blood outlet portion.

26 Claims, 15 Drawing Sheets

(51) Int. Cl.
*A61M 1/16* (2006.01)
*A61N 1/362* (2006.01)

(52) U.S. Cl.
CPC ............... *A61M 2202/0283* (2013.01); *A61M 2205/054* (2013.01)

(56) References Cited

U.S. PATENT DOCUMENTS

| | | |
|---|---|---|
| 7,122,027 B2 | 10/2006 | Trescony et al. |
| 7,171,263 B2 | 1/2007 | Darvish et al. |
| 7,190,997 B1 | 3/2007 | Darvish et al. |
| 7,294,334 B1 | 11/2007 | Michal et al. |
| 2002/0055710 A1 | 5/2002 | Tuch |
| 2002/0138048 A1 | 9/2002 | Tuch |
| 2002/0183682 A1 | 12/2002 | Darvish et al. |
| 2002/0183686 A1 | 12/2002 | Darvish et al. |
| 2003/0009127 A1 | 1/2003 | Trescony et al. |
| 2004/0086569 A1 | 5/2004 | Sparer et al. |
| 2006/0085064 A1 | 4/2006 | Tuch |
| 2006/0228452 A1 | 10/2006 | Cromack et al. |
| 2006/0228453 A1 | 10/2006 | Cromack et al. |
| 2006/0240070 A1 | 10/2006 | Cromack et al. |
| 2007/0259017 A1 | 11/2007 | Francis |
| 2008/0051871 A1 | 2/2008 | Tuch |
| 2009/0216317 A1 | 8/2009 | Cromack et al. |
| 2012/0095383 A1* | 4/2012 | Radojicic ............... A61L 27/227 604/8 |

OTHER PUBLICATIONS

Gaylor, Membrane oxygenators: current developments in design and application, J. Biomed. Eng., vol. 10, 541-547 (1988).
Lim, The history of extracorporeal oxygenators, Anaesthesia, vol. 61, 984-995 (2006).
M. M. Markowitz, D. A. Boryta, Harvey Stewart Jr., "Lithium Perchlorate Oxygen Candle. Pyrochemical Source of Pure Oxygen", Ind. Eng. Chem. Prod. Res. Dev., 1964, 3 (4), pp. 321-330.
Amann et al., "Reliability of old and new ventricular fibrillation detection algorithms for automated external defibrillators", BioMedical Engineering Online, 4:60 (2005), doi:10.1186/1475-925X-4-60.
Iwata et al., "Iodide Protects Heart Tissue from Reperfusion Injury", PLOS ONE, vol. 9, 11, pp. 1-6, e112458 (2014).
Ehlenbach et al., "Epidemiologic Study of In-Hospital Cardiopulmonary Resuscitation in the Elderly", N. Engl J. Med. vol., 361, 1, pp. 22-31 (2006).
Bardy et al., "An Entirely Subcutaneous Implantable Cardioverter-Defibrillator", N. Engl J. Med.vol., 363, 1, pp. 36-44 (2010).
Hoffmann-La Roche et al., "Creatine and Creatinine Metabolism", Physiological Reviews, vol. 80, 3, pp. 1107-1213 (2000).

* cited by examiner

IMPLANTABLE HEART TREATMENT SYSTEMS, DEVICES, AND METHODS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, an implantable heart treatment device includes, but is not limited to, a substrate configured for implantation within a body; an electromagnetic signal generator coupled to the substrate and configured to generate one or more electric signals configured to stimulate one or more tissues of a heart within the body; and an oxygenator coupled to the substrate and configured to supply one or more oxygenated molecules to one or more tissues of the heart within the body, the oxygenator including a blood inlet portion, a blood outlet portion, and an oxygen exchange portion positioned between the blood inlet portion and the blood outlet portion, the oxygen exchange portion including a high surface area oxygen exchanger configured to transfer one or more oxygenated molecules from the high surface area oxygen exchanger to blood passing from the blood inlet portion to the blood outlet portion.

In an aspect, an implantable heart treatment device includes, but is not limited to, a substrate configured for implantation within a body; an electromagnetic signal generator coupled to the substrate and configured to generate one or more electric signals configured to stimulate one or more tissues of a heart within the body; a metabolic molecule supply device coupled to the substrate and configured to supply one or more metabolic molecules to one or more tissues of the heart within the body; and control circuitry operably coupled to the electromagnetic signal generator and the metabolic molecule supply device, the control circuitry configured to generate one or more control signals according to at least a first control protocol and a second control protocol, the control circuitry configured to generate one or more control signals that cause the electromagnetic signal generator to generate the one or more electric signals upon execution of the first control protocol, the control circuitry configured to generate one or more control signals that cause the electromagnetic signal generator to generate the one or more electric signals and to generate one or more control signals that cause the metabolic molecule supply device to supply the one or more metabolic molecules upon execution of the second control protocol.

In an aspect, an implantable heart treatment device includes, but is not limited to, a substrate configured for implantation within a body; an electromagnetic signal generator coupled to the substrate and configured to generate one or more electric signals configured to stimulate one or more tissues of a heart within the body; and an energy-carrier molecule delivery portion configured to supply one or more non-oxygen cellular energy sources to one or more tissues of the heart within the body.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
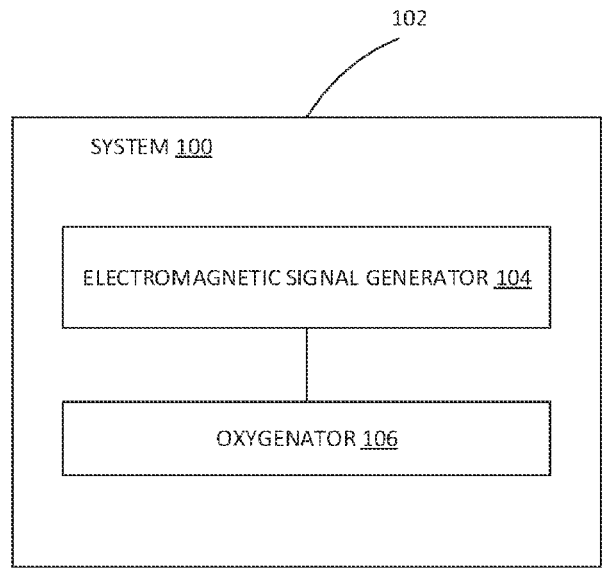
FIG. 1 is a schematic of an implantable heart treatment device in accordance with one or more embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. As used herein, the words "configured" and "adapted" are interchangeable unless the context dictates otherwise.

Systems and devices are described for treating cardiac tissue via an implantable heart treatment device that utilizes one or more mechanisms for therapy, including, but not limited to, electric stimulation, oxygenation, energy transport, and chemical species delivery. Cardiovascular disease remains the leading cause of deaths globally, with approximately 300,000 Americans dying annually from "sudden cardiac death," primarily from severe and prolonged ventricular fibrillation. On average, a human ventricular-fibrillating heart exhausts its entire myoglobin-based oxygen reserve in a fifty to seventy-five second time-frame after the blood pressure drops at the top of the coronary artery tree. Afterwards, the cardiac tissue is so "stunned" that attempts to re-start or resynchronize via electric defibrillator are statistically likely to fail. The myocardium is unable to function following the fifty to seventy-five second time-frame unless the condition is remediated. However, clinical records indicate that external cardiopulmonary resuscitation is typically insufficient for such remediation, which often results in death of a patient. In an embodiment, the systems and devices described herein may be used to treat cardiac tissue during or following a fibrillation event with electric stimulation and one or more of oxygenation, energy transport, and chemical species delivery.

In embodiments, the systems and devices described herein employ a substrate configured for implantation within a body, such as proximate cardiac tissue of the heart. The substrate can support, or have coupled thereto, an electromagnetic signal generator and one or more of an oxygenator, a metabolic molecule supply device, and an energy-carrier molecule delivery portion. In embodiments, an implantable heart treatment device includes control circuitry employing at least two control protocols for action to the cardiac tissue, with a first control protocol causing activation of an electromagnetic signal generator, and with a second control protocol causing activation of an electromagnetic signal generator and a metabolic molecule supply device.

As used herein, a "fibrillation event" includes a ventricular fibrillation event. Ventricular fibrillation is a cause of cardiac arrest and sudden cardiac death. The ventricular muscle fibers contract randomly causing a complete failure of ventricular function. Most cases of ventricular fibrillation occur in patients with pre-existing known heart disease but the precise nature of the underlying cause of ventricular fibrillation is not currently known. In an embodiment, shown in FIG. 1, a system (or device) 100 is configured to treat cardiac tissue, such as cardiac tissue during and following a fibrillation event. The system 100 includes, but is not limited to, a substrate 102, an electromagnetic signal generator 104, and an oxygenator 106. In embodiments, the substrate 102 is configured for implantation within a body of an individual and to house or support other portions of the system 100. The structure of the substrate 102 can conform to a surface of a body portion next to which or within which the system 100 is configured to reside. In embodiments, portions of the system 100 and the substrate 102 which are exposed to the individual's body comprise one or more biocompatible materials, for example, stainless steel, titanium, nitinol, gold, biocompatible ceramics, stainless steel, shape memory material, biocompatible polymer, polyester, polyamide, polytetrafluoroethylene, polyalkenes, polyethylene, ultra-high molecular weight polyethylene, copolymers or composites thereof, and the like. In embodiments, at least a portion of the substrate 102 is configured as a housing hermetically sealed from the external environment (e.g., the interior of the individual's body).

The electromagnetic signal generator 104 is coupled to the substrate 102 and is configured to generate one or more time varying electric signals configured to stimulate one or more tissues of the heart within the individual's body. In embodiments, the electromagnetic signal generator 104 includes one or more of a pacemaker device, a defibrillator device (e.g., an implantable cardioverter-defibrillator), an anti-tachycardia device, or other device configured to affect one or more physiological properties of the heart via electric signals. In embodiments, the electromagnetic signal generator 104 is configured to generate one or more time varying electric signals for the electric treatment of cardiac symptoms resulting from cardiac disease or disorder, including but not limited to myocarditis, cardiomyopathy, cardiogenic shock, congenital defect, cardiac arrest, and the like. In embodiments, the electromagnetic signal generator 104 includes an electrode configured to contract the cardiac tissues upon application of one or more electric signals. For instance, the electrode can be positioned on an exterior surface of the substrate 102, configured for contact with one or more cardiac tissues. In embodiments, the electrode includes one or more electrode leads projecting from the electromagnetic signal generator 104 or the substrate 102 to affect cardiac tissue located remotely from the electromagnetic signal generator 104 or the substrate 102. In embodiments, the electromagnetic signal generator 104 is powered by a power source including at least one of a battery, a capacitor, a thermoelectric generator, a piezoelectric generator, a microelectromechanical systems (MEMS) generator, and a biomechanical-energy harvesting generator. In an embodiment, the biomechanical-energy harvesting generator is configured to generate power based on a blood flow of the individual in which the system 100 is implanted.

The oxygenator 106 is coupled to the substrate 102 and is configured to supply one or more oxygenated molecules to one or more tissues of the heart of the individual in which the system 100 is implanted. In embodiments, the oxygenator 106 is a blood-gas exchanger having an exchange membrane configured to regulate an exchange of oxygenated molecules between the oxygenator 106 and a flow of blood through the oxygenator 106. For example, in an embodiment, shown in FIG. 2, the oxygenator 106 includes a blood inlet portion 200, an oxygen exchange portion 202, and a blood outlet portion 204. The blood inlet portion 200 is configured to receive blood from the individual in which the system 100 is implanted into the oxygenator 106 to provide the blood-gas exchange interface. The blood outlet portion 204 is configured to return oxygenated blood to the individual following the blood-gas exchange in the oxygen exchange portion 202, such as by delivery to a vein, delivery to an artery, delivery directly within the heart, and the like. The blood inlet portion 200 and the blood outlet portion 204 can include various fluid-flow passageways and ports suitable for the transport of blood, and can include, but are not limited to, biocompatible capillary conduits/tubes and micron-scale conduits/tubes (e.g., sufficient to transport at least one red blood cell through the interior of the tube). In embodiments, the conduits of the system 100 have a minimum internal diameter of greater than 10 microns to accommodate the passage of red blood cells. For example, in embodiments, at least a portion of the conduits of the system 100 have a minimum internal diameter of between 10 microns and 12 microns to accommodate the passage of red blood cells through the system 100. The internal diameter can be larger or smaller than this range, due to manufacturing tolerances, design specifications dependent on types of red blood cells, and so forth, to accommodate the passage of red bloods cells, such as in a flow of singular red bloods cells.

The source of the blood to be received by the blood inlet portion 200 and the destination of the oxygenated blood to be returned by the blood outlet portion 204 can depend on design characteristics of the system 100, including size of the substrate 102, number of inlets of the blood inlet portion 200, number of outlets of the blood outlet portion 204, portion of cardiac tissue to be treated, presence or absence of a blood pump, and so forth. The source of the blood to be received by the blood inlet portion 200 and the destination of the oxygenated blood to be returned by the blood outlet portion 204 can include sources and destinations employed for extracorporeal membrane oxygenators (see, e.g., Hung, Vuylsteke, and Valchanov, Extracorporeal Membrane Oxygenation: Coming to an ICU Near You, J. Intensive Care Society., Vol. 13, 31-38 (2012), which is incorporated herein by reference).

For example, in an embodiment, the blood inlet portion 200 includes one or more ports configured to receive blood from one or more cardiac veins, such as from one or more of the great cardiac vein (e.g., left coronary vein), the middle cardiac vein, the small cardiac vein, and at least one of the anterior cardiac veins (e.g., anterior veins of right ventricle); the blood is then oxygenated by the oxygen exchange portion 202 (described herein below), and subsequently returned by the blood outlet portion 204 having at least one port positioned within at least one coronary artery, such as within a portion of one or more of the left coronary artery, the right coronary artery, and one or more subendocardial artery.

In an embodiment, the blood inlet portion 200 includes one or more ports in contact with blood from an internal jugular vein, and configured to receive blood from one or more of the superior vena cava (SVC) and the inferior vena cava (IVC), where after oxygenation of the blood occurs in the oxygen exchange portion 202, the oxygenated blood is returned to the individual via a port of the blood outlet portion 204 positioned within at least one coronary artery, such as within a portion of one or more of the left coronary artery, the right coronary artery, and one or more subendocardial artery. The blood inlet portion 200 can include at least two ports, with at least one port positioned to receive blood from the superior vena cava (SVC) and at least one port positioned to receive blood from the inferior vena cava (IVC).

In an embodiment, the blood inlet portion 200 includes one or more ports in contact with blood from an internal jugular vein, and configured to receive blood from one or more of the superior vena cava (SVC) and the inferior vena cava (IVC), where after oxygenation of the blood occurs in the oxygen exchange portion 202, the oxygenated blood is returned to the individual via a port of the blood outlet portion 204 positioned within or proximate to the right atrium of the heart. The blood inlet portion 200 can include at least two ports, with at least one port positioned to receive blood from the superior vena cava (SVC) and at least one port positioned to receive blood from the inferior vena cava (IVC).

In an embodiment, the blood inlet portion 200 includes a port in contact with blood from an internal jugular vein, and is configured to receive blood from one or more of the superior vena cava (SVC) and the inferior vena cava (IVC), where after oxygenation of the blood occurs in the oxygen exchange portion 202, the oxygenated blood is returned to the individual via a port of the blood outlet portion 204 positioned within or proximate to one or more of the ascending aorta, the descending aorta, and the aortic arch.

In an embodiment, the blood inlet portion 200 includes a port in contact with blood from at least one of the pulmonary artery and the right ventricle, where after oxygenation of the blood occurs in the oxygen exchange portion 202, the oxygenated blood is returned to the individual via a port of the blood outlet portion 204 positioned within or proximate to one or more of the pulmonary vein, and the left atrium. In an embodiment, the blood inlet portion 200 includes a port in contact with blood from at least one of the ascending aorta, the descending aorta, the aortic arch, and the left ventricle, where after oxygenation of the blood occurs in the oxygen exchange portion 202, the oxygenated blood is returned to the individual via a port of the blood outlet portion 204 positioned within or proximate to one or more of the superior vena cava, the inferior vena cava, and the right atrium. In an embodiment, the blood inlet portion 200 includes a port in contact with blood from at least one of the ascending aorta, the descending aorta, the aortic arch, and the left ventricle, where after oxygenation of the blood occurs in the oxygen exchange portion 202, the oxygenated blood is returned to the individual via a port of the blood outlet portion 204 positioned within or proximate to one or more of the pulmonary vein, and the left atrium. In an embodiment, the blood inlet portion 200 includes a port in contact with blood from at least one of the descending aorta, the mesenteric artery, the iliac artery, and the femoral artery, where after oxygenation of the blood occurs in the oxygen exchange portion 202, the oxygenated blood is returned to the individual via a port of the blood outlet portion 204 positioned within or proximate to one or more of the femoral vein, the iliac vein, the abdominal vena cava, the inferior vena cava, and the right atrium. Other configurations are possible and are not limited to the above-provided configurations.

In some embodiments, the oxygenator 106 includes a blood pump 208. The blood pump 208 may be coupled to the blood inlet portion 200, and may be used to force blood through the oxygen exchange portion 202 (e.g., overcoming the flow resistance through high surface area oxygen exchanger 206, described further herein). In some embodiments, the blood pump 208 may be controlled so as to match the pressure at the blood outlet portion 204 to that of the blood in the destination lumen. Blood pump 208 may include the same type of blood pumps (e.g., centrifugal types, or roller types) typically used in conjunction with extracorporeal membrane oxygenators. Unlike pumps used in implantable "artificial hearts," the blood pump 208 can be configured to operate only for short durations, i.e., during a fibrillation event. The blood pump 208 may facilitate operation of embodiments where the blood inlet portion 200 is coupled to a vein or a heart atrium, and may be optional in some embodiments (e.g., embodiments where the blood inlet portion 200 is coupled to an artery or heart ventricle).

In some embodiments, the oxygenator 106 includes a controllable valve 210. The valve 210 may be coupled to the blood inlet portion 200, and may be closed during normal situations to prevent blood flow through the oxygenator (e.g., through oxygen exchange portion 202), and opened only during fibrillation events.

Figure 2:
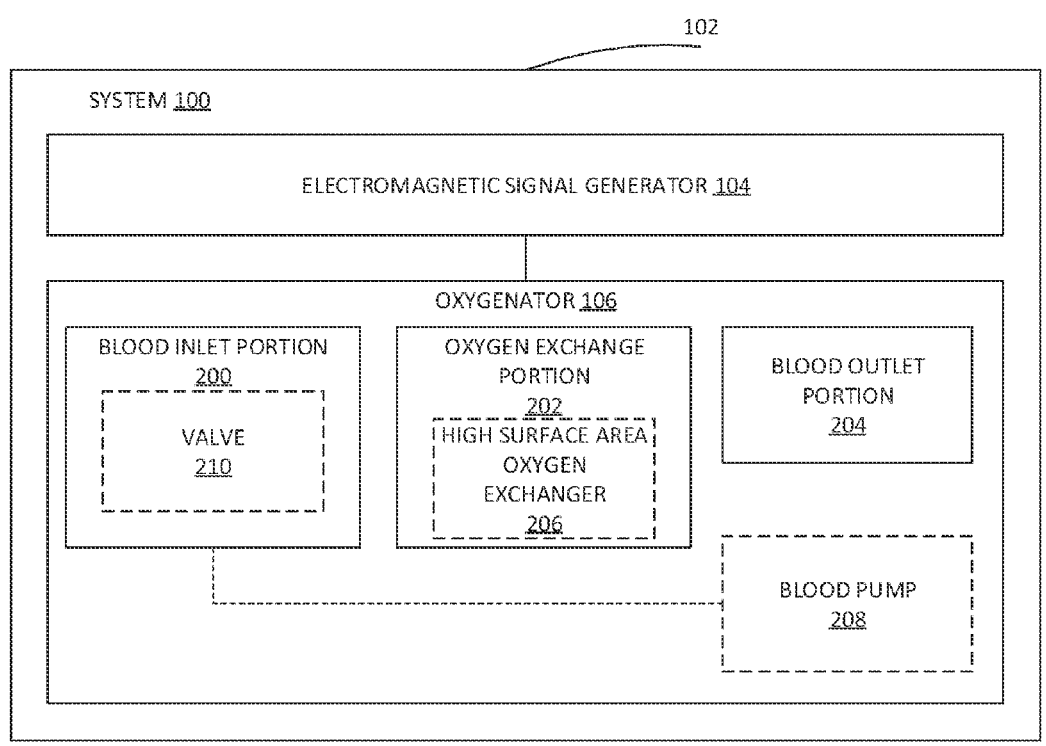
FIG. 2 is a schematic of an embodiment of a device such as shown in FIG. 1.

The oxygen exchange portion 202 of the oxygenator 106 includes a blood-gas interface for blood-gas exchange to oxygenate the blood received by the blood inlet portion 200. As shown in FIG. 2, the oxygen exchange portion 202 includes a high surface area oxygen exchanger 206 as a blood-gas interface to transfer one or more oxygenated molecules from the high surface area oxygen exchanger 206 to blood passing from the blood inlet portion 200 to the blood outlet portion 204. As used herein, the term "high surface area" is used with a context of a surface area configured for the exchange of materials, where the surface area is between approximately 0.001 square meters ($m^2$) and approximately 5 square meters ($m^2$), where the surface area can vary depending on manufacturing tolerances, material specifications, and so forth (see, e.g., Gaylor, Membrane oxygenators: current developments in design and application, J. Biomed. Eng., Vol. 10, 541-547 (1988), which is incorporated herein by reference). In general, the high surface area oxygen exchanger 206 facilitates gas exchange between the blood and gas phases by providing a significant surface area for oxygen diffusion into and through the blood phase, resulting in an oxygenated blood stream. In embodiments, the high surface area oxygen exchanger 206 includes a membrane-based oxygenator, where the membrane is an oxygen-permeable membrane that is permeable to the oxygenated molecules, but not to the blood. The oxygen can permeate through the membrane based on concentration gradients, where the blood can include a lower oxygen concentration, thereby facilitating diffusion of the oxygenated molecules through the membrane and into the blood.

In embodiments, the membrane includes a plurality of hollow fibers through which blood or oxygenated molecules are passed, where the material that is not included in the hollow fibers (i.e., the corresponding oxygenated molecules or blood) is passed along the exterior of the hollow fibers. The number of hollow fibers utilized generally depends on the desired surface area of the high surface area oxygen exchanger 206, the size of the hollow fibers, the material of the hollow fibers, and so forth. In embodiments, the high surface area oxygen exchanger 206 includes between approximately one thousand and ten million hollow fibers. In embodiments, the hollow fibers are constructed from biocompatible materials, including but not limited to, silicone, polypropylene, and polymethylpentene (e.g., 4-methyl-1-pentene, PMP), and can include one or more coatings thereon, including but not limited to, heparin and silicone (see, e.g., Lim, The history of extracorporeal oxygenators, Anaesthesia, Vol. 61, 984-995 (2006), which is incorporated herein by reference). In embodiments, the hollow fibers are constructed from polypropylene, which can include micropores in the polypropylene structure. The micropores are configured to permit the diffusion of gas through the pores to oxygenate the blood that flows through the fibers, or that is flowing on an exterior of the fiber (e.g., an inverse-flow configuration). In embodiments, the hollow fibers are constructed from polymethylpentene (PMP), which is a gas permeable polymer material, through which the oxygenated material can pass to the blood located in the interior or on the exterior of the hollow fibers.

Figure 3A:
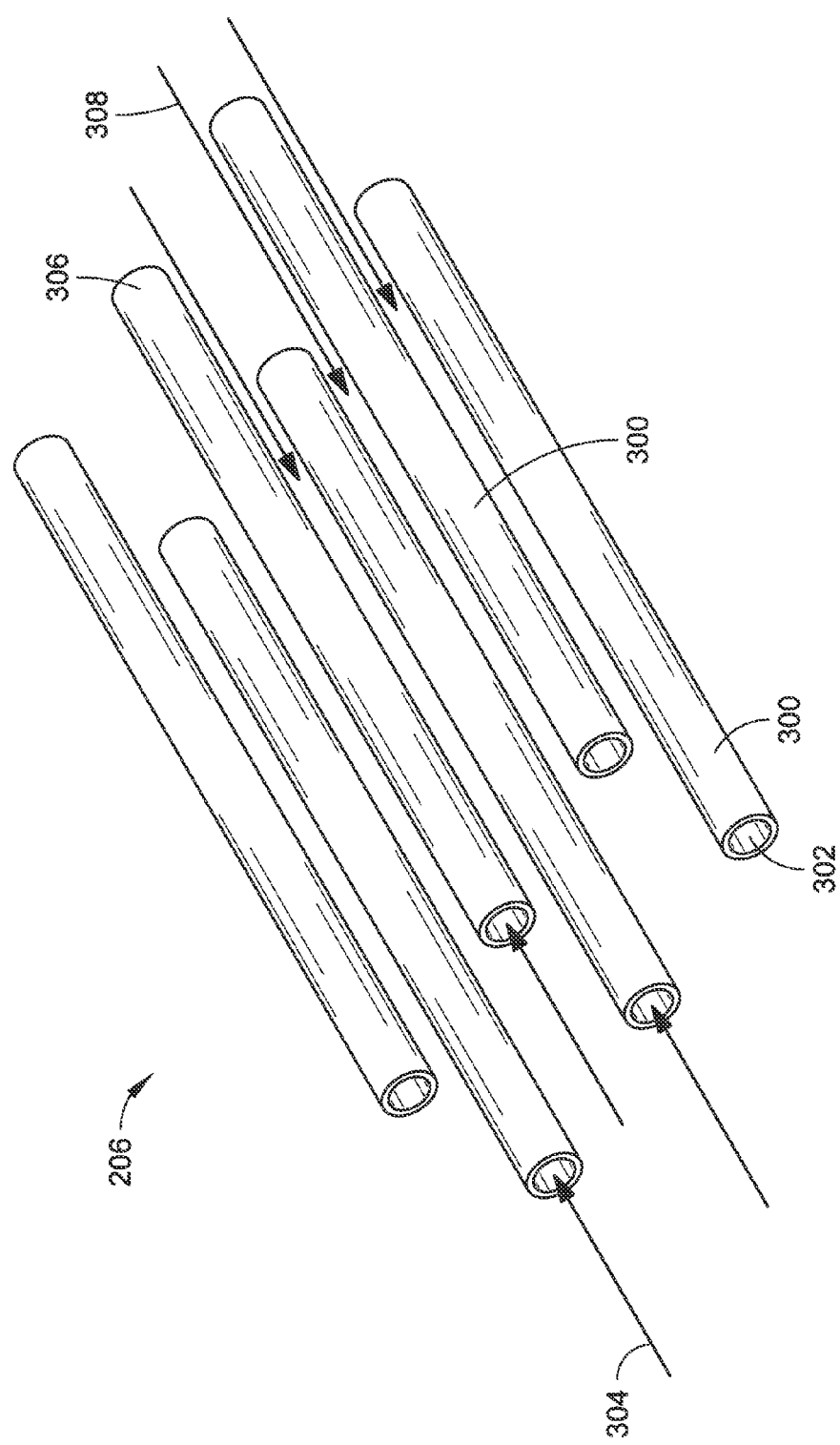
FIG. 3A is a schematic of an embodiment of a device such as shown in FIG. 1.
Figure 3B:
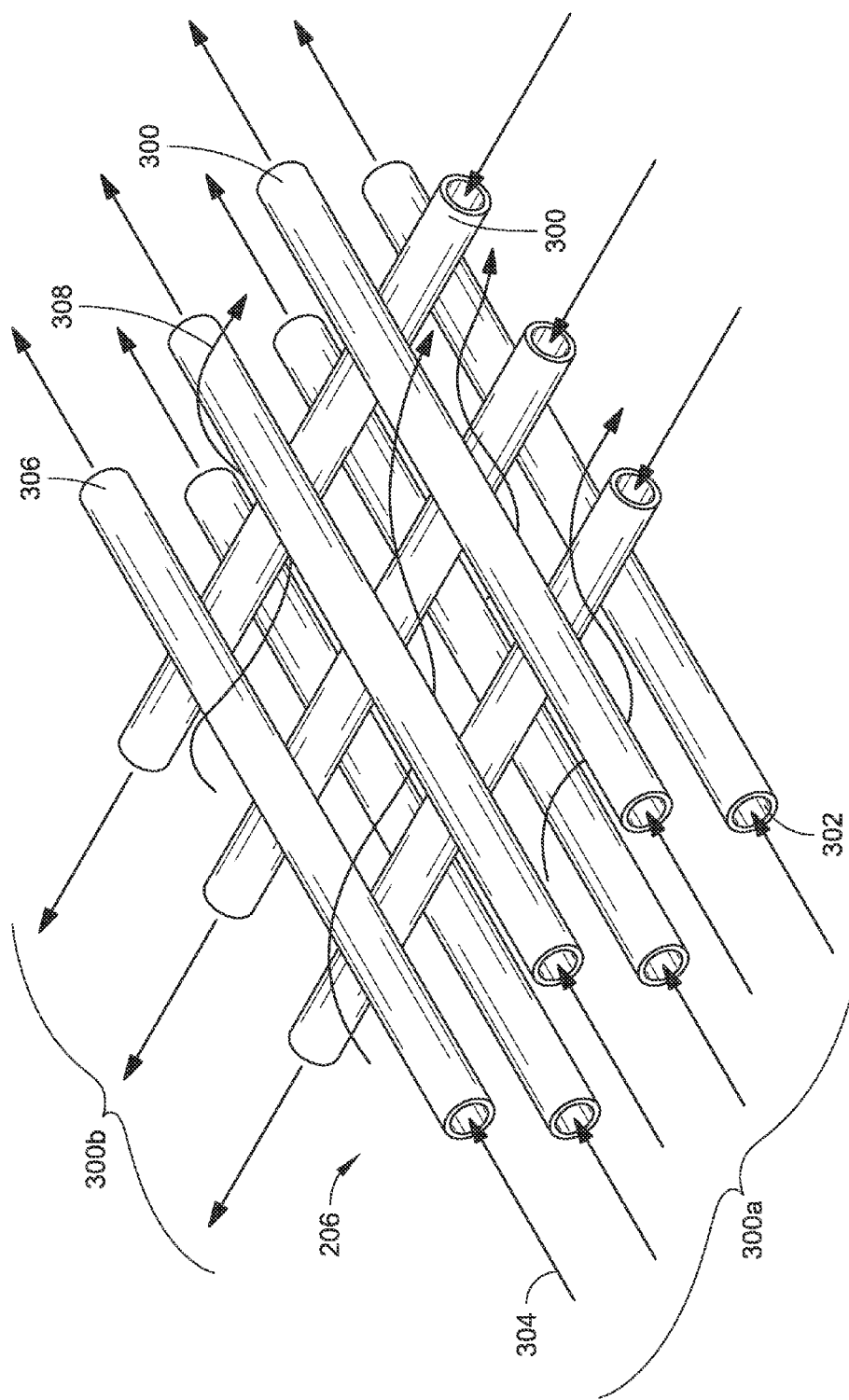
FIG. 3B is a schematic of an embodiment of a device such as shown in FIG. 1.

Referring to FIG. 3A, the high surface area oxygen exchanger 206 includes a plurality of hollow fibers 300 arranged in a shell and tube configuration having oxygenated material (e.g., a flow of oxygenated gas) through the interior 302 of the hollow fibers 300 (flow shown as 304). Blood is passed over the exterior 306 of the hollow fibers 300 (flow shown as 308). Alternatively, the blood can be passed through the interior 302 of the hollow fibers 300, where the oxygenated material would then pass over the exterior 306 of the hollow fibers. Referring to FIG. 3B, the high surface area oxygen exchanger 206 includes a plurality of hollow fibers 300 arranged in a cross-flow configuration, where a first set of hollow fibers 300a are arranged substantially perpendicularly to a second set of hollow fibers 300b. Each of the first set of hollow fibers 300a and the second set of hollow fibers 300b include a flow of oxygenated material through the interior of the 302 of the hollow fibers 300 (flow shown as 304). Blood is passed over the exterior 306 of the hollow fibers 300 of the first set of hollow fibers 300a and the second set of hollow fibers 300b (flow shown as 308). The cross-flow configuration can facilitate mixing of the blood for efficient gas diffusion through the blood, to oxygenate the blood with the oxygenated material transported through the micropore structure of the hollow fibers 300. Alternatively, the blood can be passed through the interior 302 of the hollow fibers 300, where the oxygenated material would then pass over the exterior 306 of the hollow fibers. While FIG. 3B shows a cross-flow configuration having an approximately ninety degree offset between the first set of hollow fibers 300a and the second set of hollow fibers 300b, other offsets can be utilized, such as for example, an offset of between forty-five and ninety degrees. In an embodiment, blood flow within the high surface area oxygen exchanger 206 resembles an artery-capillary-vein geometry, involving passage through a low-pressure drop supply manifold coupled to the blood inlet portion 200 (the "artery" analog), short flow passages through or around an array of hollow fibers 300 in the oxygen exchange portion 202 (the "capillary" analog), and then passage through a low-pressure drop return manifold coupled to the blood outlet portion 204 (the "vein" analog). In an embodiment, use of 20 micron diameter hollow fibers in a 25% fill-factor array results in a volume for the oxygen exchange portion 202 of 20 $cm^3$ for a membrane surface area of 1 $m^2$. Utilization of an equal volume for the supply and return manifolds results in a 40 $cm^3$ volume for the high surface area oxygen exchanger 208.

Figure 4A:
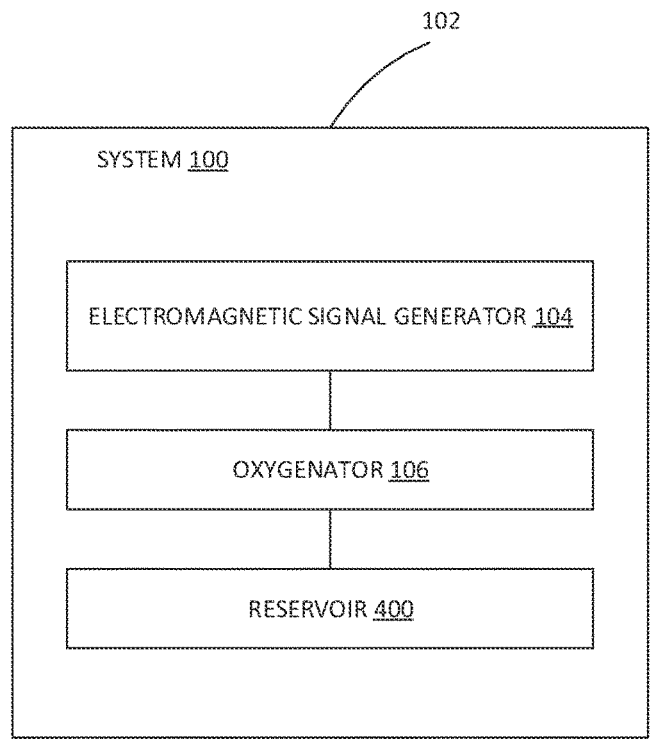
FIG. 4A is a schematic of an embodiment of a device such as shown in FIG. 1.
Figure 4B:
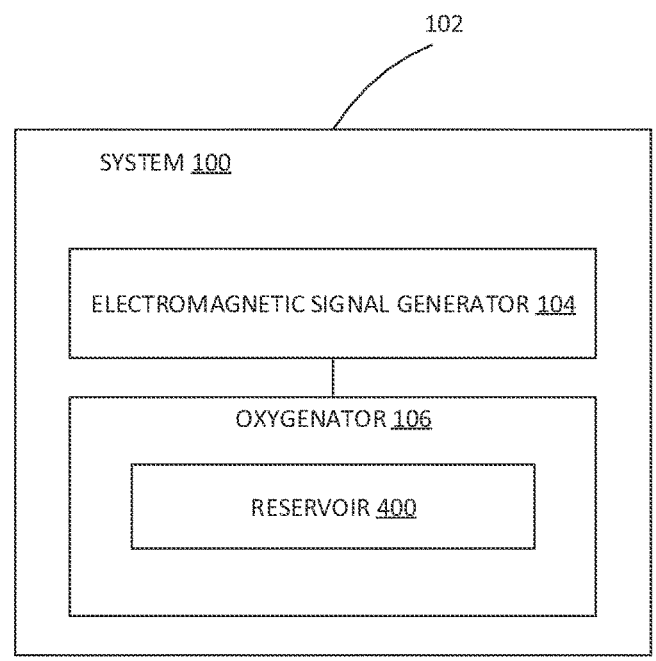
FIG. 4B is a schematic of an embodiment of a device such as shown in FIG. 1.
Figure 5A:
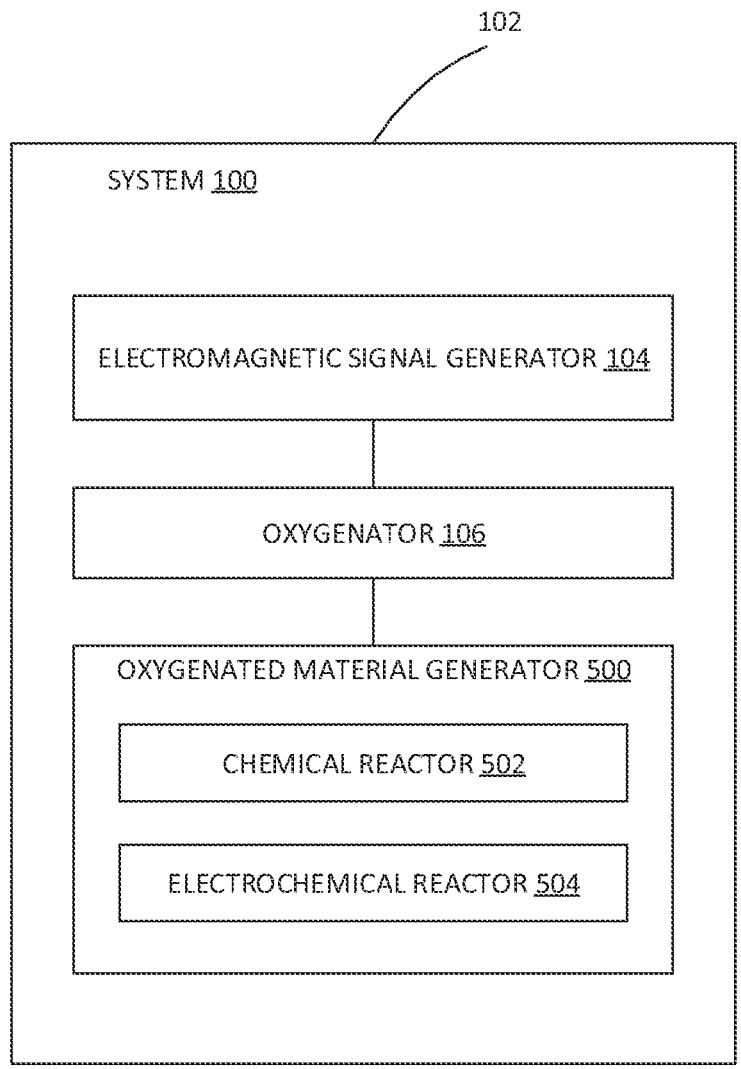
FIG. 5A is a schematic of an embodiment of a device such as shown in FIG. 1.
Figure 5B:
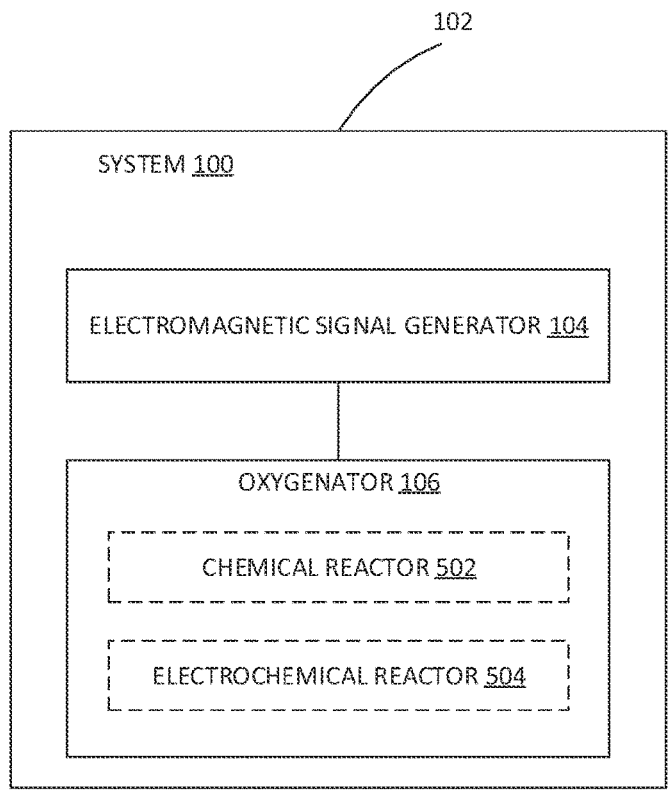
FIG. 5B is a schematic of an embodiment of a device such as shown in FIG. 1.

In embodiments, the oxygenated molecules are stored in vivo in the system 100, generated in vivo by the system 100, or a combination of stored in and generated by the system 100. For example, referring to the embodiment shown in FIG. 4A, the system includes a reservoir 400 in fluid communication with the oxygenator 106. The reservoir 400 is configured to store the oxygenated material within the reservoir and to supply the oxygenated material to the oxygenator 106. The supply of the oxygenated material from the reservoir 400 to the oxygenator 106 can be regulated by control circuitry, such as for example, by regulating a valve or port between the reservoir 400 and the oxygenator 106. Alternatively or additionally, the system can include reservoir 400 as a component of the oxygenator 106, as shown in FIG. 4B. In embodiments, such as the embodiment shown in FIG. 5, the system 100 includes an oxygenated material generator 500 configured to generate the oxygenated material within the system 100, which can include one or more of a chemical reactor 502 and an electrochemical reactor 504. The chemical reactor 502 is configured to generate the oxygenated material as a product of a chemical reaction occurring within the system 100 (or within the oxygenator 106, as shown in FIG. 5B). For example, the chemical reaction can include, but is not limited to, an alkali metal combustion with peroxide (e.g., lithium combustion with peroxide, degradation of hydrogen peroxide), absorption of carbon dioxide with an alkali metal oxide (e.g., $Li_2O_2$), and so forth. For example, the chemical reaction can include a reaction of sodium chlorate, barium peroxide, and potassium chlorate (as used in some chemical oxygen generators for aircraft, available for example from Molecular Products America). For example, the chemical reactor 502 can include an oxygen candle (i.e., a chlorate candle). A discussion of oxygen candles is presented in "Lithium Perchlorate Oxygen Candle. Pyrochemical Source of Pure Oxygen", by M. M. Markowitz, D. A. Boryta, Harvey Stewart Jr., *Ind. Eng. Chem. Prod. Res. Dev.*, 1964, 3 (4), pp 321-330 (which is incorporated herein by reference). In embodiments, the chemical reactor 502 includes thermal insulation to limit exposure of body tissue to thermal energy associated with chemical oxygen generation. In embodiments, the chemical reactor 502 includes a catalyst configured to facilitate the chemical reaction. The electrochemical reactor 504 is configured to generate the oxygenated material as a product of an electrochemical reaction occurring within the system 100 (or within the oxygenator 106, as shown in FIG. 5B). For example, the electrochemical reaction can include, but is not limited to, electrolysis of water to generate gaseous oxygen. The electrochemical reaction can include other oxygen-generating electrochemical reactions including, but not limited to, $Ag_2O$ with $I_2$, $Na_2O$ with $I_2$, $Ag_2O$ with S, and other electrochemical reactions disclosed in U.S. Pat. No. 7,122,027 (which is incorporated herein by reference). In embodiments, the oxygenated material is generated on demand, such as regulated by control circuitry, for immediate use by the oxygenator, or can be generated in advance of requiring its use, where the oxygenated material is stored until needed. In embodiments, the oxygenated material is adsorbed to a surface of the high surface area oxygen exchanger 206, such as, for example, the interior 302 or exterior 306 of the hollow fibers 300.

In embodiments, the oxygenated molecules that are transferred between the oxygenator 106 and the blood include one or more carrier molecules configured to transport gaseous oxygen (e.g., $O_2$). A carrier molecule can include an individual molecule (e.g., a perflurocarbon) or can include a multi-molecular structure (e.g., a liposome or micelle). For example, the carrier molecules utilized by the oxygenator 106 can include, but are not limited to, liposomes, micelles, and perflurocarbons. In embodiments, the oxygenated molecules within the associated carrier molecules are stored in the reservoir 400, for use by the oxygenator 106 to transfer one or more of the oxygen stored therein and carrier molecule with the oxygenated molecule.

In embodiments, the system 100 is configured to activate one or more of the electromagnetic signal generator 104 and the oxygenator 106 as directed by control signals from control circuitry. For example, in an embodiment, shown in FIG. 6, the system 100 includes control circuitry 600 configured to provide one or more control signals to the electromagnetic signal generator 104 and the oxygenator 106 for activation of the respective devices. In embodiments, the control circuitry 600 generates the control signals based on measurements from one or more physiological parameter sensors (also called "physiological sensors" herein). The physiological parameter sensors can be resident, i.e., included as a component of the system 100 (e.g., shown as physiological sensor 602 in FIG. 6), located remotely from the system 100, or a combination of resident and remote sensors, and such sensors can measure a physiological parameter representative of a condition of the heart. In embodiments, the physiological sensor includes a blood pressure sensor configured to measure a sudden blood pressure drop of an aortic region, a coronary artery, a cardiac vein, and the like to determine whether the heart is undergoing a fibrillation event. For example, the physiological sensor can measure the blood pressure at the aortic arch to determine whether the heart is undergoing a fibrillation event. In embodiments, the physiological sensor includes an oxygenation sensor configured to measure a cardiac oxygenation level, such as an oxygenation level of cardiac tissue-based myoglobin. In embodiments, the physiological sensor includes one or more electrodes configured to measure a heart electrical activity level, such as the temporal and spatial progression of a heart's depolarization wave; for example an ECG or EKG. When a fibrillation event is detected by the physiological sensor, the physiological sensor (or associated control circuitry) can provide an indication (e.g., in the form of sense signals, control signals, and so forth) to the control circuitry 600 regarding the fibrillation event. This indication can include, but is not limited to, whether a fibrillation event is occurring, the current duration of the fibrillation event, and the like. In embodiments, an ECG is performed by utilizing sense signals from the physiological sensors to determine whether a heart is undergoing ventricular fibrillation. Such determinations can be based on detection algorithms that differentiate between various cardiac states indicative of cardiac arrest, such as ventricular fibrillation, and cardiac states that may not be indicative of cardiac arrest or that do not require electric stimulation or treatment, such as a fast but stable sinus rhythm, a heart that recently underwent successful defibrillation, and so forth. The detection algorithms can include, but are not limited to, a threshold crossing interval (TCI) algorithm, an autocorrelation (ACF) algorithm, a ventricular fibrillation filter (VF filter) algorithm, a spectral algorithm, a complexity measure algorithm, a standard exponential (STE) algorithm, a modified exponential algorithm (MEA), a signal comparison algorithm (SCA), a wavelet based algorithm, a Li algorithm, and a Tompkins algorithm (see, e.g., Amann et al., Reliability of old and new ventricular fibrillation detection algorithms for automated external defibrillators, BioMedical Engineering Online, 4:60 (2005), doi:10.1186/1475-925X-4-60, which is incorporated herein by reference). The control circuitry 600 can then provide control signals to one or more of the electromagnetic signal generator 104 and the oxygenator 106 for treatment of the cardiac tissue during the fibrillation event. In embodiments, the control circuitry 600 is configured to make a determination regarding whether a fibrillation event is occurring, a current duration of a fibrillation event, and the like based on one or more sense signals received from the physiological sensors. In embodiments, the control circuitry 600 provides control signals to the electromagnetic signal generator 104, independent of the oxygenator 106. In embodiments, the control circuitry 600 provides control signals to each of the electromagnetic signal generator 104 and the oxygenator 106.

Figure 6:
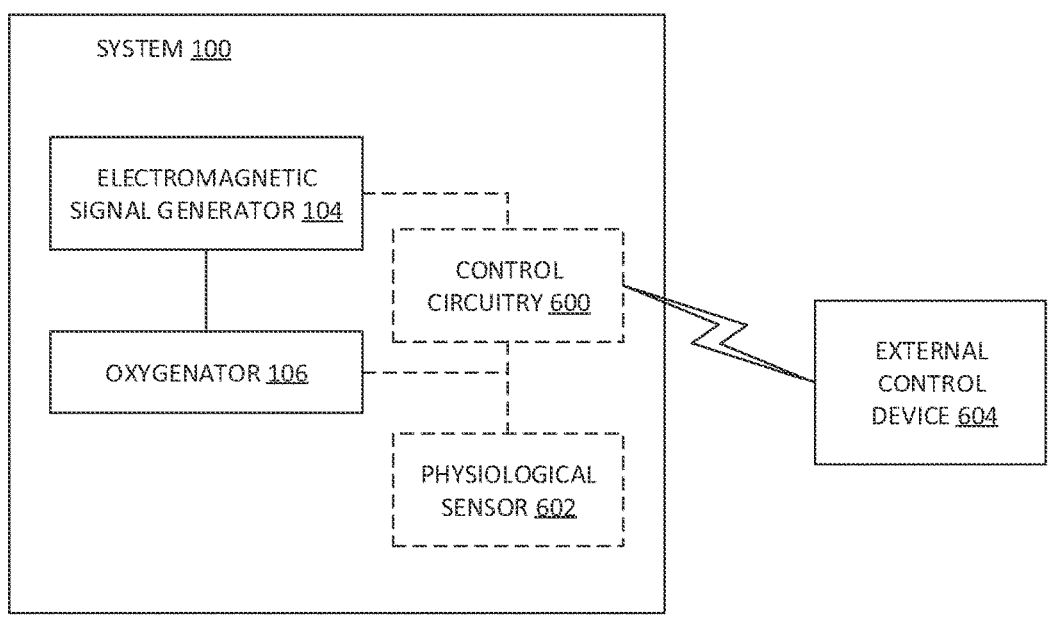
FIG. 6 is a schematic of an embodiment of a device such as shown in FIG. 1.

In embodiments, the control circuitry 600 generates the control signals based on commands issued by an external control device (shown as 604 in FIG. 6). In embodiments, the control circuitry 600 is a resident component that is coupled to the substrate 102. In embodiments, the control circuitry 600 can send and receive signals between external control device 604 via associated wireless communication methods including, but not limited to acoustic communication signals, optical communication signals, radio communication signals, infrared communication signals, ultrasonic communication signals, and the like. The control circuitry 600 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

In embodiments, the oxygenator 106 is configured to supply one or more materials to the blood in addition to the oxygenated molecules. For example, the materials in addition to the oxygenated molecules can include, but are not limited to, hydrogen sulfide ($H_2S$), carbon dioxide ($CO_2$), carbon monoxide (CO), nitric oxide (NO), nitrous oxide ($N_2O$), nitrogen dioxide ($NO_2$), and iodide (e.g., iodide ions ($I^-$) and salts thereof (e.g., sodium iodide (NaI)), see, e.g., Iwata et al., Iodide Protects Heart Tissue from Reperfusion Injury, PLOS ONE, Vol. 9, 11, e112458 (2014), which is incorporated herein by reference). These materials can be used to protect the cardiac tissue from injury (e.g., ischemia reperfusion injury) during and after a fibrillation event, to control metabolic processes of cardiac tissue during and after a fibrillation event, to provide localized or systemic anesthetic, and so forth.

Figure 7:
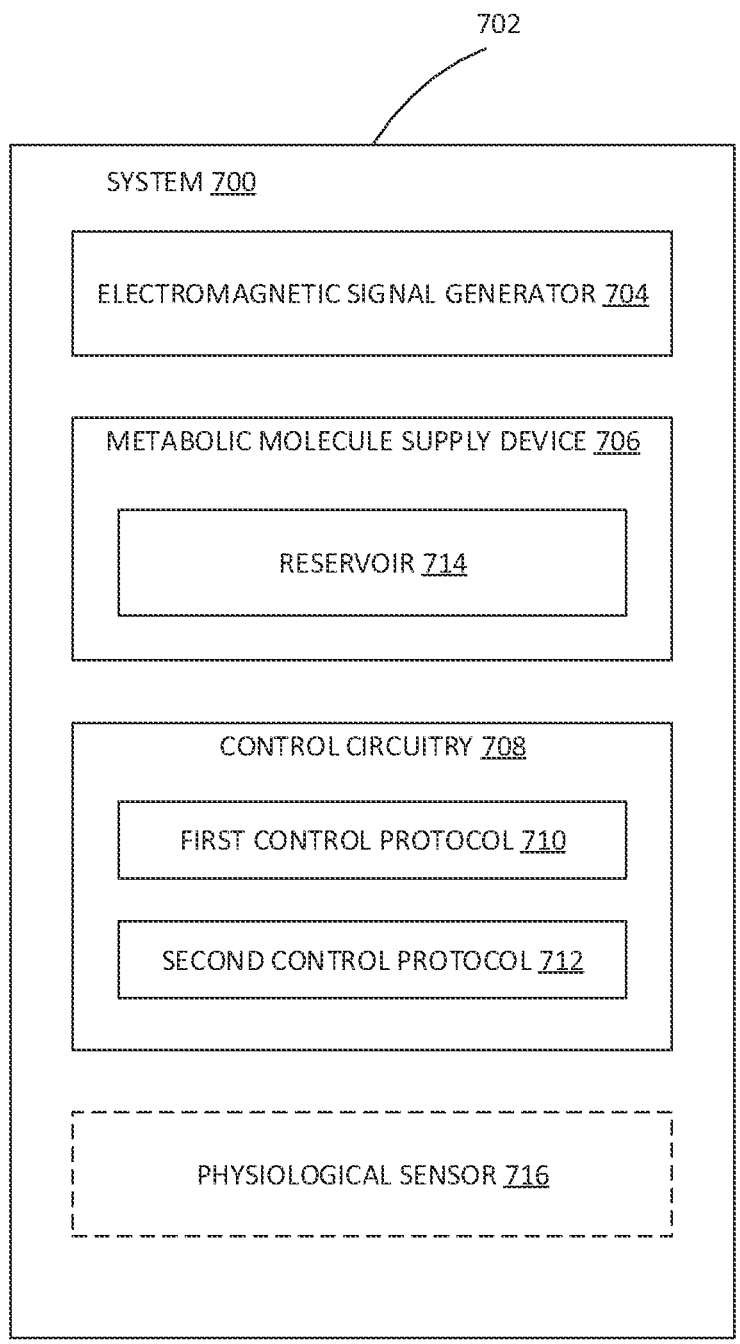
FIG. 7 is a schematic of an implantable heart treatment device in accordance with one or more embodiments.

In an embodiment, shown in FIG. 7, a system (or device) 700 is configured to treat cardiac tissue, such as cardiac tissue during and following a fibrillation event. The system 700 includes, but is not limited to, a substrate 702, an electromagnetic signal generator 704, a metabolic molecule supply device 706, and control circuitry 708 configured to execute a first control protocol 710 and a second control protocol 712. While two control protocols are shown, the control circuitry 708 is not limited to two control protocols, and can execute more than two, as desired. The substrate 702 is configured for implantation within a body of an individual and to house or support other portions of the system 700. In embodiments, the structure of the substrate 702 is similar to, or the same as, the structure of the substrate 102 described herein, with corresponding functionalities. The electromagnetic signal generator 704 is coupled to the substrate 702 and is configured to generate one or more electric signals configured to stimulate one or more tissues of the heart within the individual's body. In embodiments, the structure of the electromagnetic signal generator 704 is similar to, or the same as, the structure of the electromagnetic signal generator 104 described herein, with corresponding functionalities.

The metabolic molecule supply device 706 is coupled to the substrate 702 and is configured to supply one or more metabolic molecules to one or more tissues of the heart within the body. The term "metabolic molecule" is used with a context for describing molecules utilized by a biological (e.g., human) body for metabolic processes, or those materials that affect the metabolic process of the body, and can include, but are not limited to, oxygenated molecules and iodide. In embodiments, the metabolic molecules are stored by the system 700 in vivo, such as in a reservoir of the system 700. In embodiments, the metabolic molecule supply device 706 includes an oxygenator, such as oxygenator 106 described herein for the transfer of oxygenated molecules between the oxygen exchange portion 202 and blood passing from the blood inlet portion 200 to the blood outlet portion 206. In embodiments, the metabolic molecule supply device 706 includes a reservoir (e.g., reservoir 714) or is in fluid communication with a reservoir, or a combination of both, where the reservoir is configured to store the metabolic molecules for use by the metabolic molecule supply device 706 to supply the one or more metabolic molecules to the cardiac tissue.

The control circuitry 708 is configured to generate one or more control signals based on execution of the first control protocol 710 and the second control protocol 712. In embodiments, upon execution by the control circuitry 708 of the first control protocol 710, the control circuitry 708 generates one or more control signals that cause the electromagnetic signal generator 704 to generate one or more electric signals configured to stimulate cardiac tissues. For example, the first control protocol 710 includes instructions that can dictate actions for the system 700 to take during a fibrillation event, but prior to substantial exhaustion (e.g., more than 25%, more than 50%, more than 75%, more than 90%) of myoglobin-based oxygen storage of the heart. In embodiments, upon execution by the control circuitry 708 of the second control protocol 712, the control circuitry 708 generates one or more control signals that cause the electromagnetic signal generator 704 to generate one or more electric signals configured to stimulate cardiac tissues and the control circuitry 708 generates one or more control signals that cause the metabolic molecule supply device 706 to supply the one or more metabolic molecules to one or more cardiac tissues. For example, the second control protocol 712 can provide direction regarding actions for the system 700 to take during an extended fibrillation event where metabolic molecules, such as oxygen are beneficial in attempting to treat a heart undergoing systemic shock associated with exhaustion of myoglobin-based oxygen storage (e.g., a period of about fifty seconds to about seventy-five seconds following onset of a fibrillation event). In embodiments, the control circuitry 708 determines which control protocol to execute based on measurements from one or more physiological sensors. The one or more physiological sensors can be included as a component of the system 700 (e.g., shown as physiological sensor 716 in FIG. 7), located remotely from the system 700, or a combination of resident and remote sensors. In embodiments, the physiological sensor is a blood pressure sensor configured to measure a blood pressure of an aortic region, a coronary artery, a cardiac vein, and the like, to determine whether the heart is undergoing a fibrillation event. For example, the physiological sensor can measure the blood pressure at the aortic arch to determine whether the heart is undergoing a fibrillation event. In embodiments, the physiological sensor includes an oxygenation sensor configured to measure a cardiac oxygenation level, such as an oxygenation level of cardiac tissue-based myoglobin. In embodiments, the physiological sensor includes one or more electrodes configured to measure a heart electrical activity level. When a fibrillation event is detected by the physiological sensor, the physiological sensor (or associated control circuitry) can provide an indication (e.g., in the form of sense signals, control signals, and so forth) to the control circuitry 708 regarding the fibrillation event. This indication can include, but is not limited to, whether a fibrillation event is occurring, the current duration of the fibrillation event, and the like. The control circuitry 708 can then provide control signals to at least one of execute the first control protocol, execute the second control protocol, cease execution of the first control protocol, and cease execution of the second control protocol. The control circuitry 708 can then provide control signals to one or more of the electromagnetic signal generator 704 and the metabolic molecule supply device 706 for treatment of the cardiac tissue during the fibrillation event. In embodiments, the control circuitry 708 provides control signals to the electromagnetic signal generator 704, independent of the metabolic molecule supply device 706, such as provided by the first control protocol 710. In embodiments, the control circuitry 708 provides control signals to each of the electromagnetic signal generator 104 and the metabolic molecule supply device 706, such as provided by the second control protocol 712.

Figure 8:
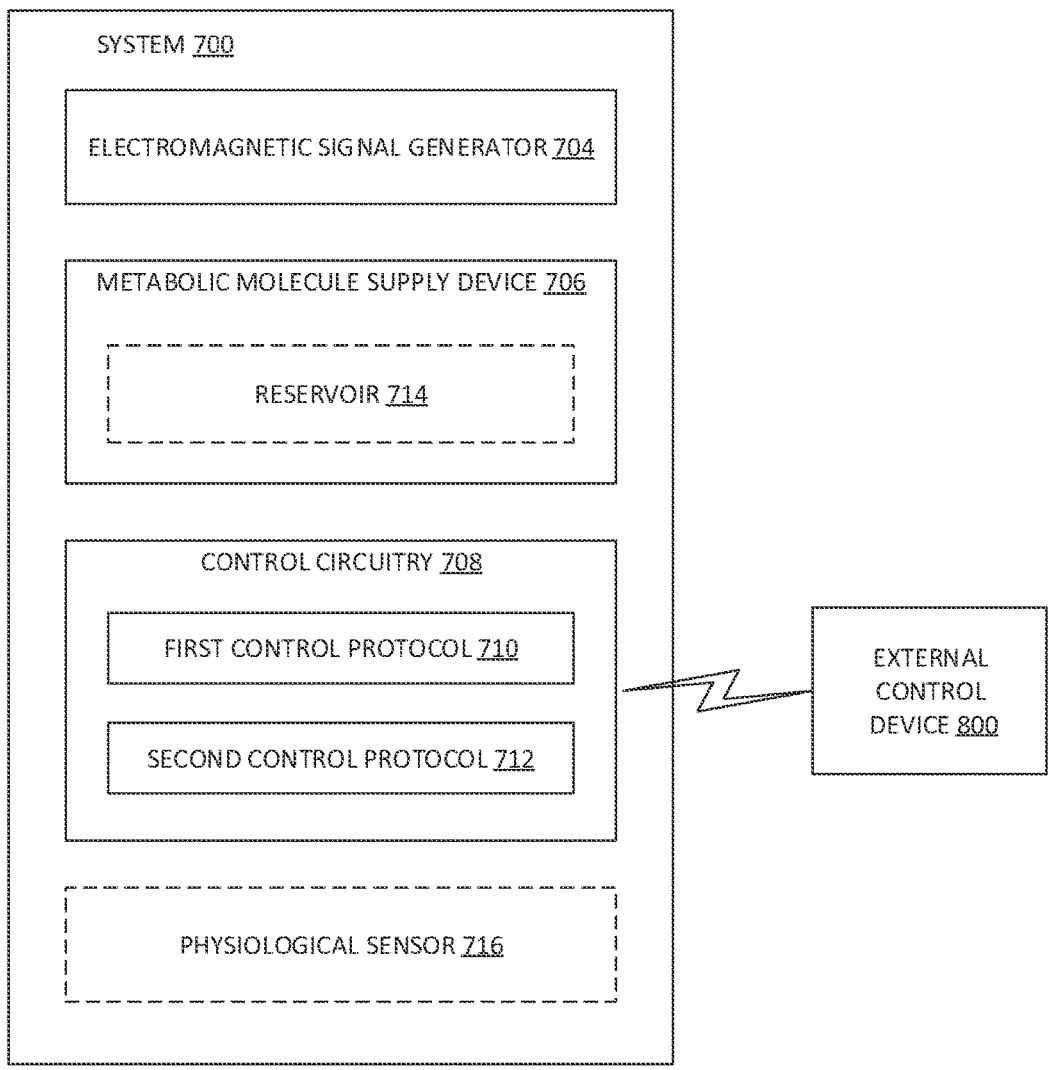
FIG. 8 is a schematic of an embodiment of a device such as shown in FIG. 7.

In embodiments, the control circuitry 708 generates the control signals based on commands issued by an external control device (shown as 800 in FIG. 8). In embodiments, the control circuitry 708 can send and receive signals between external control device 800 via associated wireless communication methods including, but not limited to acoustic communication signals, optical communication signals, radio communication signals, infrared communication signals, ultrasonic communication signals, and the like. The control circuitry 708 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands. In embodiments, the control circuitry 708 can wirelessly transmit the control signals or information associated with the control signals to an external device, e.g., to report control circuitry actions.

In embodiments, the control circuitry 708 is configured to receive one or more control signals from the external control device 800 and to make a determination regarding a defibrillation state. For example, the control circuitry 708 can receive one or more control signals from the external control device 800, whereby the control circuitry 708 directs one or more physiological sensors to measure a physiological parameter associated with cardiac activity (e.g., blood pressure, blood oxygenation level, myoglobin oxygenation level, and the like, which can be representative of a condition of the heart) to determine a defibrillation state of the individual in which the system 700 is implanted. Based upon the physiological parameter of the heart, the control circuitry 708 can execute the first control protocol 710 or the second control protocol 712. For example, in embodiments, when the physiological parameter of the heart indicates a fibrillation event is occurring, and the myoglobin-based oxygen is not exhausted (e.g., a period between onset of a fibrillation event and between approximately fifty seconds and seventy-five seconds following the onset of the fibrillation event), the control circuitry 708 executes the first control protocol 710, resulting in activation of the electromagnetic signal generator 704 for electric stimulation of the cardiac tissue. In embodiments, when the physiological parameter of the heart indicates a fibrillation event is occurring, and the myoglobin-based oxygen is substantially exhausted (e.g., a period of fifty seconds to seventy-five seconds following onset of a fibrillation event), the control circuitry 708 executes the second control protocol 712, resulting in activation of each of the electromagnetic signal generator 704 and the metabolic molecule supply device 706 for treatment of the cardiac tissue, such as through electric stimulation of the cardiac tissue and delivery of oxygenated molecules to the cardiac tissue. In some embodiments, execution of one or more of the control protocols can be based on a predetermined time period. For example, execution of the first control protocol can be carried out for 50 seconds, followed by commencement of the second control protocol. For example, execution of the second control protocol can be carried out for 90 seconds, after which it is stopped; it may then optionally be re-executed based on sensing of one or more physiological parameters.

Figure 9:
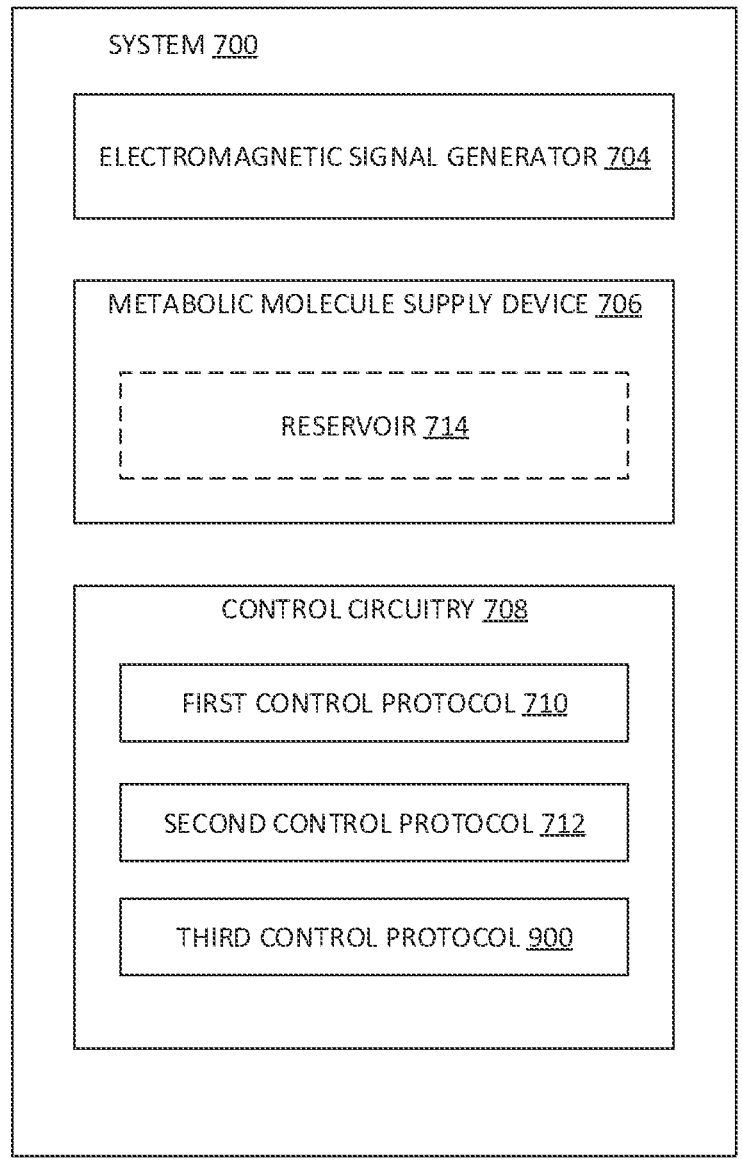
FIG. 9 is a schematic of an embodiment of a device such as shown in FIG. 7.

In an embodiment, shown in FIG. 9, the control circuitry 708 of the system 700 further includes a third control protocol 900. The third control protocol 900 can relate to determining whether and when to administer iodide to the heart, such as by dictating whether and when to generate one or more control signals that cause the metabolic molecule supply device 706 to supply iodide (or one or more salts thereof) to cardiac tissue. Iodide provides benefits from reperfusion injury suffered by heart tissue from acute myocardial infarction (see, e.g., Iwata et al., incorporated by reference herein). For instance, heart tissue is temporarily deprived of oxygen during an acute myocardial infarction, causing a decrease in oxygen consumption in an attempt to regulate oxygen levels. When blood flow is restored post reperfusion, oxygen consumption can increase to levels several fold higher than before the ischemic event. This excessive oxygen consumption period can cause damage to heart tissue, such as inflammation and cell death. Iodide can perform a therapeutic role regarding cardiac tissue damage resulting from reperfusion. In embodiments, the control circuitry 708 is configured to execute the third control protocol 900 upon detection of a fibrillation event to cause the control circuitry 708 to generate one or more control signals that cause the metabolic molecule supply device 706 to supply iodide to cardiac tissue. In embodiments, the control circuitry 708 is configured to execute the third control protocol 900 prior to execution of the first control protocol 710 and the second control protocol 712. For example, since each of the first control protocol 710 and the second control protocol 712 are directed to providing electric stimulation of cardiac tissue, which could result in reperfusion of blood to heart tissue, the supply of iodide to the cardiac tissue prior to reperfusion of blood can aid in protecting the heart tissue from ischemia reperfusion injury.

In embodiments, the system 700 is configured to supply one or more non-oxygen cellular energy sources to one or more tissues of the heart. For example, in an embodiment, the metabolic molecule supply device 706 is configured to supply one or more non-oxygen cellular energy sources to one or more tissues of the heart, such by introducing the one or more non-oxygen cellular energy sources to an interface between a blood stream and the metabolic molecule supply device 706. In embodiments, the one or more non-oxygen cellular energy sources can include, but are not limited to adenosine triphosphate (ATP), cyclic adenosine monophosphate (cAMP), adenosine monophosphate (AMP), adenosine diphosphate (ADP), creatine, and cyclocreatine. In embodiments, the one or more non-oxygen cellular energy sources are supplied as a result of execution by the control circuitry 708 of one or more of the first control protocol 710, the second control protocol 712, the third control protocol 900, and another control protocol.

Figure 10:
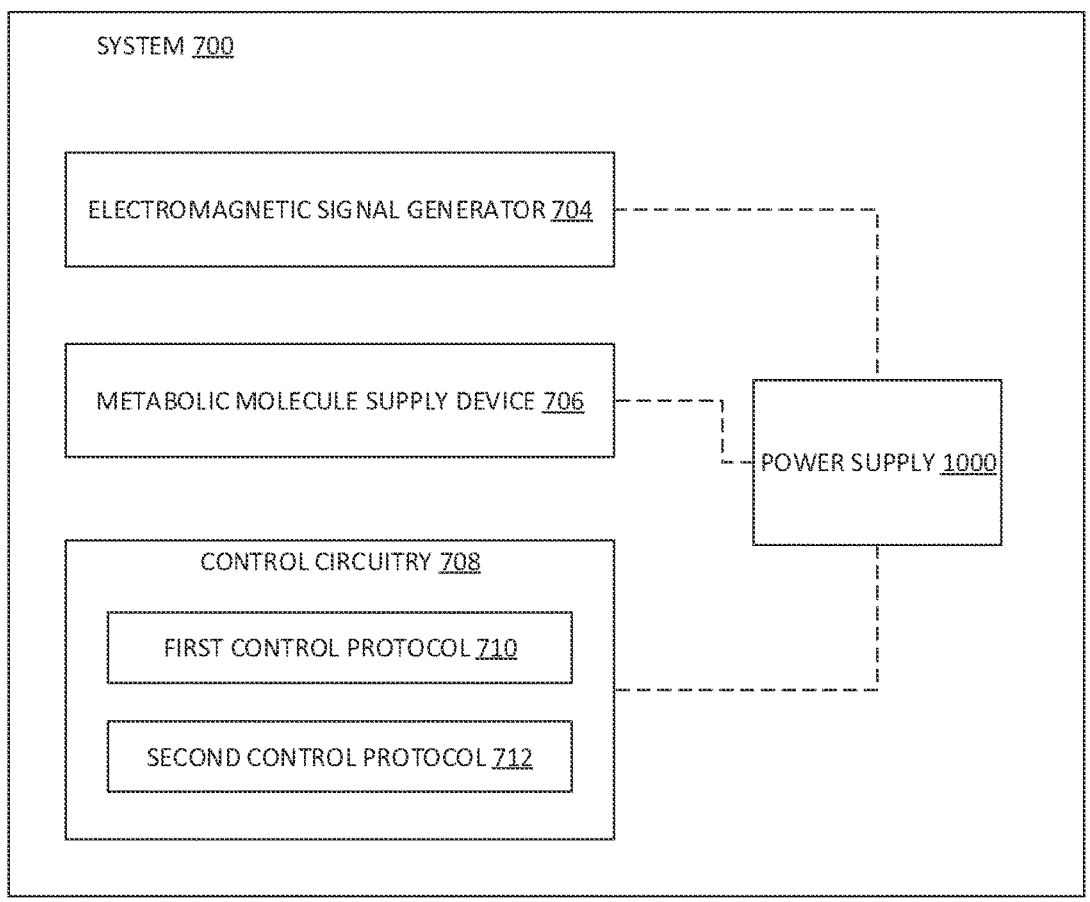
FIG. 10 is a schematic of an embodiment of a device such as shown in FIG. 7.

The systems 100 and 700 can include one or more power sources configured to provide power to one or more components of the systems. For example, in embodiments, as shown in FIG. 10, the system 700 includes a power supply 1000 configured to provide power to one or more components of the system 700 including, but not limited to, the electromagnetic signal generator 704, the metabolic molecule supply device 706, and the control circuitry 708. In embodiments, the power supply 1000 is a resident device component that is coupled to the substrate 702. Examples of resident device components include, but are not limited to, batteries (e.g., a thin film battery, a microbattery) and solar cells (e.g., silicon-based solar cells) configured to convert light energy into electrical energy for use by the components of the systems described herein. In embodiments, the power supply 1000 includes one or more components positioned remotely from the substrate 702 that transmit power signals via associated wireless power methods including, but not limited to, inductive coupling of power signals. In such embodiments, the system 700 includes one or more components positioned on the substrate 702 configured to one or more of receive, process, and/or distribute the power signals that originate from components positioned remotely from the substrate 702. For example, the system 700 can include a wireless power coil coupled to the substrate 702 that is configured to receive a remote power signal, such as a remote power signal originating from a remote transmission coil.

Figure 11A:
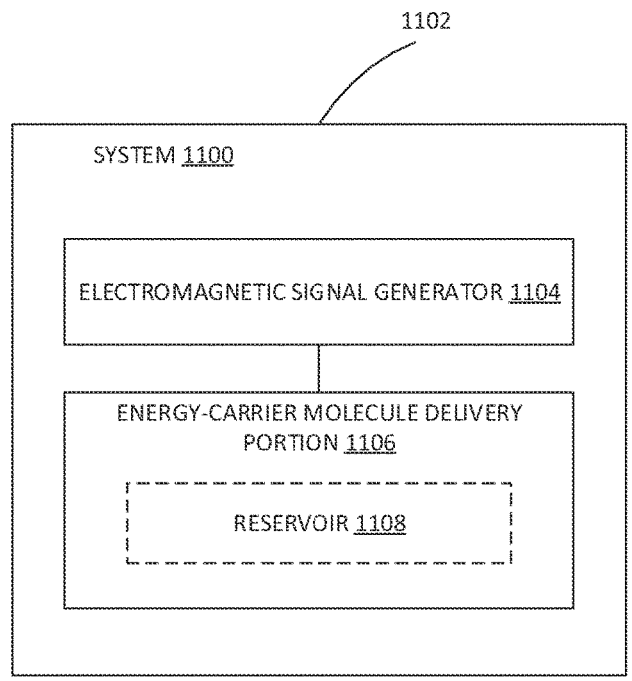
FIG. 11A is a schematic of an implantable heart treatment device in accordance with one or more embodiments.

In an embodiment, shown in FIG. 11A, a system (or device) 1100 is configured to treat cardiac tissue, such as cardiac tissue during and following a fibrillation event. The system 1100 includes, but is not limited to, a substrate 1102, an electromagnetic signal generator 1104, and an energy-carrier molecule delivery device 1106. The substrate 1102 is configured for implantation within a body of an individual and to house or support other portions of the system 1100. In embodiments, the structure of the substrate 1102 is similar to, or the same as, the structure of the substrates 102 and 702 described herein, with corresponding functionalities. The electromagnetic signal generator 1104 is coupled to the substrate 1102 and is configured to generate one or more electric signals configured to stimulate one or more tissues of the heart within the individual's body. In embodiments, the structure of the electromagnetic signal generator 1104 is similar to, or the same as, the structure of the electromagnetic signal generators 104 and 704 described herein, with corresponding functionalities.

The energy-carrier molecule delivery device 1106 is coupled to the substrate 1102 and is configured to supply one or more non-oxygen cellular energy sources to one or more tissues of the heart within the body. In embodiments, the one or more non-oxygen cellular energy sources can include, but are not limited to adenosine triphosphate (ATP), cyclic adenosine monophosphate (cAMP), adenosine monophosphate (AMP), adenosine diphosphate (ADP), creatine, and cyclocreatine. In embodiments, the non-oxygen cellular energy sources include one or more carrier molecules configured to transport the non-oxygen cellular energy source (e.g., ATP). The carrier molecules can include, but are not limited to, liposomes, micelles, and perflurocarbons. In embodiments, the carrier molecules include a targeting agent configured to target cardiac tissues, such as ischemic cardiac tissues. The targeting agent can include, but is not limited to an antibody, an aptamer, and the like, configured to bind to a distinct target protein. In embodiments, the carrier molecules include an endocytosis-promoting agent. The endocytosis-promoting agent can include, but is not limited to, a clathrin, a liposome, a transferrin, a growth factor, an antibody, an aptamer, and the like. In embodiments, the energy-carrier molecule delivery device 1106 includes a reservoir (e.g., reservoir 1108) or is in fluid communication with a reservoir, or a combination of both, where the reservoir is configured to store the non-oxygen cellular energy sources for use by the energy-carrier molecule delivery device 1106 to supply the one or more non-oxygen cellular energy sources to the cardiac tissue.

Figure 11B:
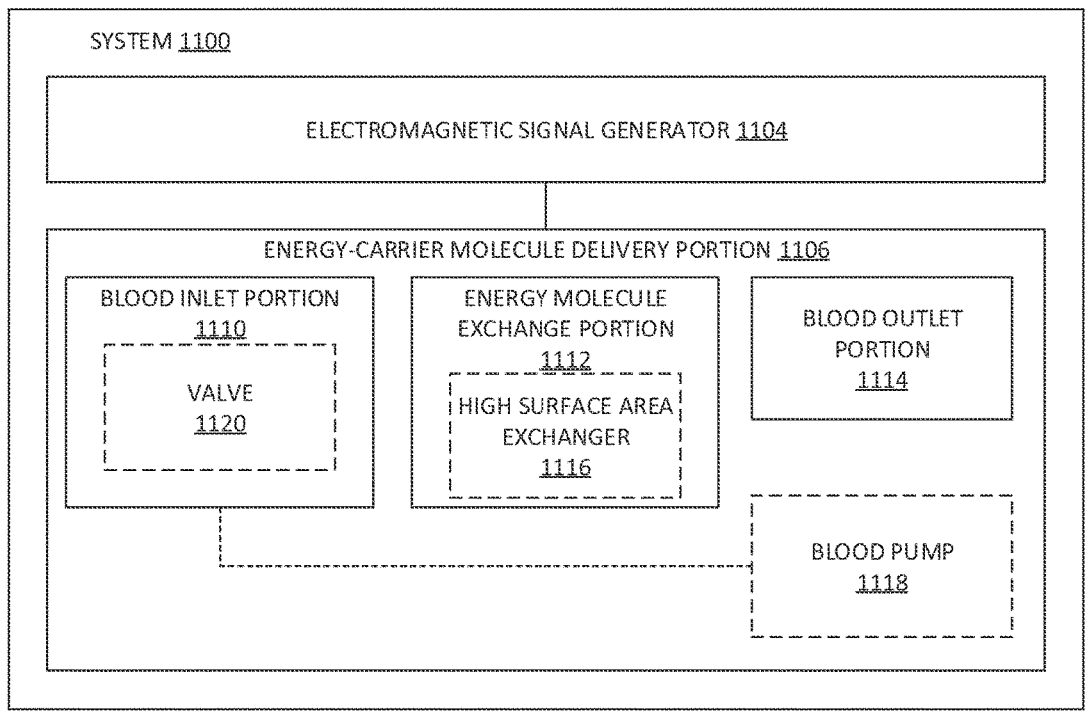
FIG. 11B is a schematic of an implantable heart treatment device in accordance with one or more embodiments.

In an embodiment, shown in FIG. 11B, the energy-carrier molecule delivery device 1106 includes a blood inlet portion 1110, an energy molecule exchange portion 1112, and a blood outlet portion 1114. The blood inlet portion 1110 is configured to receive blood from the individual in which the system 1100 is implanted into the energy-carrier molecule delivery device 1106 to provide a blood-energy-carrier molecule exchange interface. The blood outlet portion 1114 is configured to return blood having the non-oxygen cellular energy sources to the individual following blood-energy-carrier molecule exchange in the energy molecule exchange portion 1112. The blood inlet portion 1110 and the blood outlet portion 1114 can include various fluid-flow passageways and ports suitable for the transport of blood, and can include, but are not limited to, biocompatible capillary conduits/tubes and micron-scale conduits/tubes (e.g., sufficient to transport at least one red blood cell through the interior of the tube or between the exterior of neighboring tubes). In embodiments, at least a portion of the conduits of the system 1100 have an internal diameter (or inter-conduit separation) of greater than 10 microns to accommodate the passage of red blood cells. For example, in embodiments, at least a portion of the conduits of the system 100 have a minimum internal diameter of between 10 microns and 12 microns to accommodate the passage of red blood cells through the system 100. The internal diameter may be larger or smaller than this range, due to manufacturing tolerances, design specifications dependent on types of red blood cells, and so forth, to accommodate the passage of red bloods cells, such as in a flow of singular red bloods cells. In embodiments, the energy molecule exchange portion 1112 includes a high surface area exchanger 1116 configured to transfer the one or more metabolic molecules to blood in contact with the high surface area exchanger 1116. In general, the high surface area exchanger 1116 facilitates exchange between the blood and metabolic molecules by providing a significant surface area for diffusion into and through the blood phase.

The source of the blood to be received by the blood inlet portion 1110 and the destination of the blood to be returned by the blood outlet portion 1114 may depend on design characteristics of the system 1100, including size of the substrate 1102, number of inlets of the blood inlet portion 1110, number of outlets of the blood outlet portion 1114, portion of cardiac tissue to be treated, presence or absence of a blood pump, and so forth. The source of the blood to be received by the blood inlet portion 1110 and the destination of the oxygenated blood to be returned by the blood outlet portion 1114 may include sources and destinations employed for extracorporeal membrane oxygenators (see, e.g., Hung, et al., ibid., incorporated herein by reference).

For example, in an embodiment, the blood inlet portion 1110 includes one or more ports configured to receive blood from one or more cardiac veins, such as from one or more of the great cardiac vein (e.g., left coronary vein), the middle cardiac vein, the small cardiac vein, and at least one of the anterior cardiac veins (e.g., anterior veins of right ventricle); the blood is then oxygenated by the energy molecule exchange portion 1112, and subsequently returned by the blood outlet portion 1114 having at least one port positioned within at least one coronary artery, such as within a portion of one or more of the left coronary artery, the right coronary artery, and one or more subendocardial artery.

In an embodiment, the blood inlet portion 1110 includes one or more ports in contact with blood from an internal jugular vein, and configured to receive blood from one or more of the superior vena cava (SVC) and the inferior vena cava (IVC), where after introduction of the non-oxygen cellular energy molecule to the blood occurs in the energy molecule exchange portion 1112, the blood is returned to the individual via a port of the blood outlet portion 1114 positioned within at least one coronary artery, such as within a portion of one or more of the left coronary artery, the right coronary artery, and one or more subendocardial artery. The blood inlet portion 1110 can include at least two ports, with at least one port positioned to receive blood from the superior vena cava (SVC) and at least one port positioned to receive blood from the inferior vena cava (IVC).

In an embodiment, the blood inlet portion 1110 includes one or more ports in contact with blood from an internal jugular vein, and configured to receive blood from one or more of the superior vena cava (SVC) and the inferior vena cava (IVC), where after introduction of the non-oxygen cellular energy molecule to the blood occurs in the energy molecule exchange portion 1112, the blood is returned to the individual via a port of the blood outlet portion 1114 positioned within or proximate to the right atrium of the heart. The blood inlet portion 1110 can include at least two ports, with at least one port positioned to receive blood from the superior vena cava (SVC) and at least one port positioned to receive blood from the inferior vena cava (IVC).

In an embodiment, the blood inlet portion 1110 includes a port in contact with blood from an internal jugular vein, and is configured to receive blood from one or more of the superior vena cava (SVC) and the inferior vena cava (IVC), where after introduction of the non-oxygen cellular energy molecule to the blood occurs in the energy molecule exchange portion 1112, the blood is returned to the individual via a port of the blood outlet portion 1114 positioned within or proximate to one or more of the ascending aorta, the descending aorta, and the aortic arch.

In an embodiment, the blood inlet portion 1110 includes a port in contact with blood from at least one of the pulmonary artery and the right ventricle, where after oxygenation of the blood occurs in the energy molecule exchange portion 1112, the oxygenated blood is returned to the individual via a port of the blood outlet portion 1114 positioned within or proximate to one or more of the pulmonary vein, and the left atrium. In an embodiment, the blood inlet portion 1110 includes a port in contact with blood from at least one of the ascending aorta, the descending aorta, the aortic arch, and the left ventricle, where after oxygenation of the blood occurs in the energy molecule exchange portion 1112, the oxygenated blood is returned to the individual via a port of the blood outlet portion 1114 positioned within or proximate to one or more of the superior vena cava, the inferior vena cava, and the right atrium. In an embodiment, the blood inlet portion 1110 includes a port in contact with blood from at least one of the ascending aorta, the descending aorta, the aortic arch, and the left ventricle, where after oxygenation of the blood occurs in the energy molecule exchange portion 1112, the oxygenated blood is returned to the individual via a port of the blood outlet portion 1114 positioned within or proximate to one or more of the pulmonary vein, and the left atrium. In an embodiment, the blood inlet portion 1110 includes a port in contact with blood from at least one of the descending aorta, the mesenteric artery, the iliac artery, and the femoral artery, where after oxygenation of the blood occurs in the energy molecule exchange portion 1112, the oxygenated blood is returned to the individual via a port of the blood outlet portion 1114 positioned within or proximate to one or more of the femoral vein, the iliac vein, the abdominal vena cava, the inferior vena cava, and the right atrium. Other configurations are possible and are not limited to the above-provided configurations.

In some embodiments, the energy-carrier molecule delivery device 1106 includes a blood pump 1118. The blood pump 1118 may be coupled to the blood inlet portion 1110, and may be used to force blood through the energy molecule exchange portion 1112 (e.g., overcoming the flow resistance through high surface area exchanger 1116). In some embodiments, the blood pump 1118 may be controlled so as to match the pressure at the blood outlet portion 1114 to that of the blood in the destination lumen. Blood pump 1118 may include the same type of blood pumps (e.g., centrifugal types, or roller types) typically used in conjunction with extracorporeal membrane oxygenators. Unlike pumps used in implantable "artificial hearts," the blood pump 1118 can be configured to operate only for short durations, i.e., during a fibrillation event. The blood pump 1118 may facilitate operation of embodiments where the blood inlet portion 1110 is coupled to a vein or a heart atrium, and may be optional in some embodiments (e.g., embodiments where the blood inlet portion 1110 is coupled to an artery or heart ventricle).

In some embodiments, the energy-carrier molecule delivery portion 1106 includes a controllable valve 1120. The valve 1120 may be coupled to the blood inlet portion 1110, and may be closed during normal situations to prevent blood flow through the energy-carrier molecule delivery portion 1106 (e.g., through energy molecule exchange portion 1112), and opened only during fibrillation events.

Figure 12:
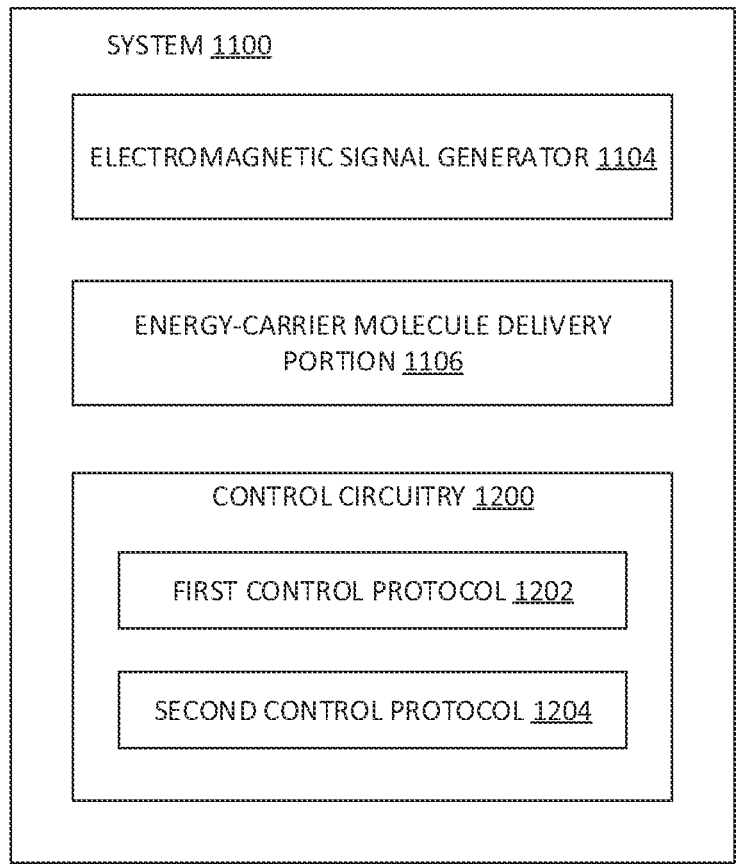
FIG. 12 is a schematic of an embodiment of a device such as shown in FIGS. 11A and 11B.

In an embodiment, shown in FIG. 12, the system 1100 includes control circuitry 1200 configured to generate one or more control signals based upon execution of one or more control protocols, such as a first control protocol 1202 and a second control protocol 1204. In embodiments, upon execution by the control circuitry 1200 of the first control protocol 1202, the control circuitry 1200 generates one or more control signals that cause the electromagnetic signal generator 1104 to generate one or more electric signals configured to stimulate cardiac tissues. For example, the first control protocol 1202 can provide direction regarding actions for the system 1100 to take during a fibrillation event. In embodiments, upon execution by the control circuitry 1200 of the second control protocol 1204, the control circuitry 1200 generates one or more control signals that cause the electromagnetic signal generator 1104 to generate one or more electric signals configured to stimulate cardiac tissues and the control circuitry 1200 generates one or more control signals that cause the energy-carrier molecule delivery device 1106 to supply the one or more non-oxygen cellular energy sources to one or more cardiac tissues. For example, the second control protocol 1204 can provide direction regarding actions for the system 1100 to take during an extended fibrillation event where non-oxygen cellular energy sources, such as ATP are beneficial in attempting to treat a heart undergoing systemic shock associated with exhaustion of myoglobin-based oxygen storage (e.g., a period of fifty seconds to seventy-five seconds following onset of a fibrillation event). In embodiments, the control circuitry 1200 determines which control protocol to execute based on measurements from one or more physiological sensors. The one or more physiological sensors can be included as a component of the system 1100, located remotely from the system 1100, or a combination of resident and remote sensors. In embodiments, the physiological sensor is a blood pressure sensor configured to measure a blood pressure of an aortic region, a coronary artery, a cardiac vein, and the like, to determine whether the heart is undergoing a fibrillation event. For example, the physiological sensor can measure the blood pressure at the aortic arch to determine whether the heart is undergoing a fibrillation event. In embodiments, the physiological sensor includes an oxygenation sensor configured to measure a cardiac oxygenation level, such as an oxygenation level of cardiac tissue-based myoglobin. When a fibrillation event is detected by the physiological sensor, the physiological sensor (or associated control circuitry) can provide an indication (e.g., in the form of sense signals, control signals, and so forth) to the control circuitry 1200 regarding the fibrillation event. This indication can include, but is not limited to, whether a fibrillation event is occurring, the current duration of the fibrillation event, and the like. The control circuitry 1200 can then provide control signals to one or more of the electromagnetic signal generator 1104 and the energy-carrier molecule delivery device 1106 for treatment of the cardiac tissue during the fibrillation event. In embodiments, the control circuitry 1200 provides control signals to the electromagnetic signal generator 1104, independent of the energy-carrier molecule delivery device 1106, such as provided by the first control protocol 1202. In embodiments, the control circuitry 1200 provides control signals to each of the electromagnetic signal generator 1104 and the energy-carrier molecule delivery device 1106, such as provided by the second control protocol 1204.

Figure 13:
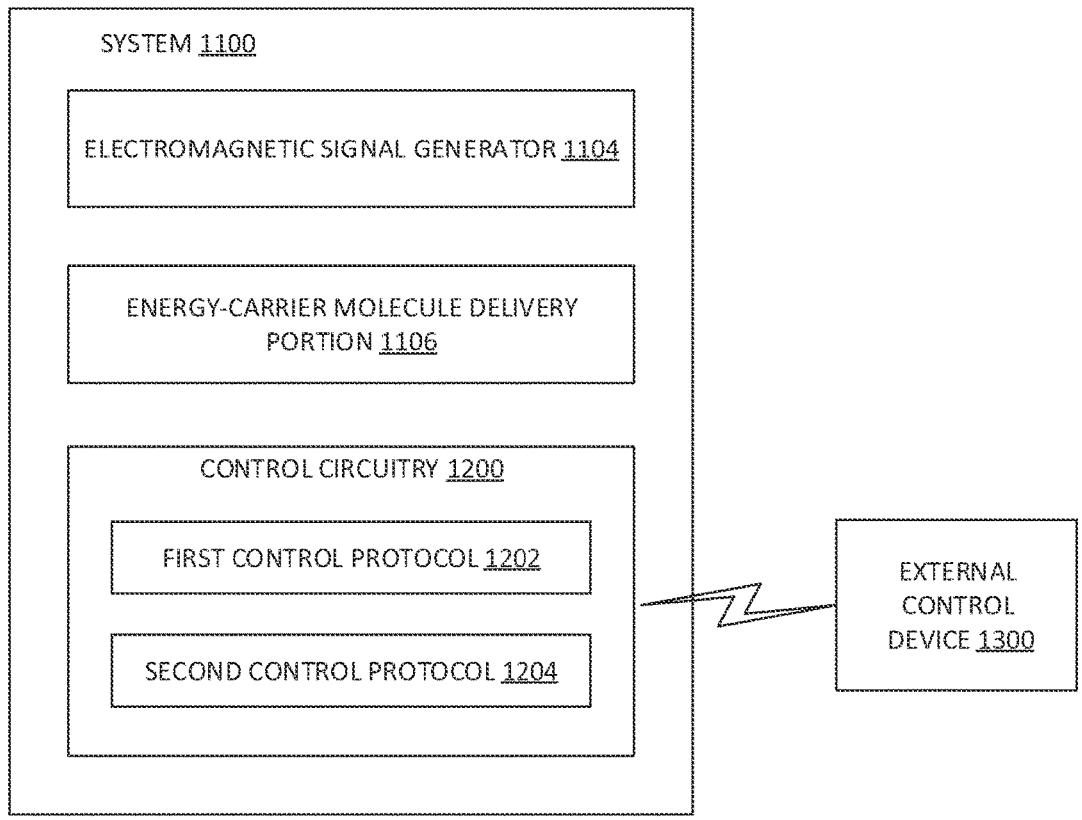
FIG. 13 is a schematic of an embodiment of a device such as shown in FIGS. 11A and 11B.

In embodiments, the control circuitry 1200 generates the control signals based on commands issued by an external control device (shown as 1300 in FIG. 13). In embodiments, the control circuitry 1200 can send and receive signals between external control device 1300 via associated wireless communication methods including, but not limited to acoustic communication signals, optical communication signals, radio communication signals, infrared communication signals, ultrasonic communication signals, and the like. The control circuitry 1200 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

In embodiments, the control circuitry 1200 is configured to receive one or more control signals from the external control device 1300 and to make a determination regarding a defibrillation state. For example, the control circuitry 1200 can receive one or more control signals from the external control device 1300, whereby the control circuitry 1200 directs one or more physiological sensors to measure a physiological parameter associated with cardiac activity (e.g., blood pressure, blood oxygenation level, myoglobin oxygenation level, and the like) to determine a defibrillation state of the individual in which the system 1100 is implanted. Based upon the physiological parameter of the heart, the control circuitry 1200 can execute the first control protocol 1202 or the second control protocol 1204. For example, in embodiments, when the physiological parameter of the heart indicates a fibrillation event is occurring, and the myoglobin-based oxygen is not exhausted (e.g., a period between onset of a fibrillation event and between approximately fifty seconds and seventy-five seconds following the onset of the fibrillation event), the control circuitry 1200 executes the first control protocol 1202, resulting in activation of the electromagnetic signal generator 1104 for electric stimulation of the cardiac tissue. In embodiments, when the physiological parameter of the heart indicates a fibrillation event is occurring, and the myoglobin-based oxygen is substantially exhausted (e.g., a period of fifty seconds to seventy-five seconds following onset of a fibrillation event, exhaustion of greater than 50%, etc.), the control circuitry 1200 executes the second control protocol 1204, resulting in activation of each of the electromagnetic signal generator 1104 and the energy-carrier molecule delivery device 1106 for treatment of the cardiac tissue, such as through electric stimulation of the cardiac tissue and delivery of non-oxygen cellular energy sources to the cardiac tissue.

In embodiments, the system 1100 is configured to supply one or more materials to the blood in addition to the non-oxygen cellular energy sources. For example, the materials in addition to the non-oxygen cellular energy sources can include, but are not limited to, hydrogen sulfide ($H_2S$), carbon dioxide ($CO_2$), carbon monoxide (CO), nitric oxide (NO), nitrous oxide ($N_2O$), and nitrogen dioxide ($NO_2$), and iodide (e.g., iodide ions ($I^-$) and salts thereof (e.g., sodium iodide (NaI)), see, e.g., Iwata et al., incorporated herein by reference). These materials can be used to protect the cardiac tissue from injury (e.g., ischemia reperfusion injury) during and after a fibrillation event, to control metabolic processes of cardiac tissue during and after a fibrillation event, to provide localized or systemic anesthetic, and so forth.

Figure 14:
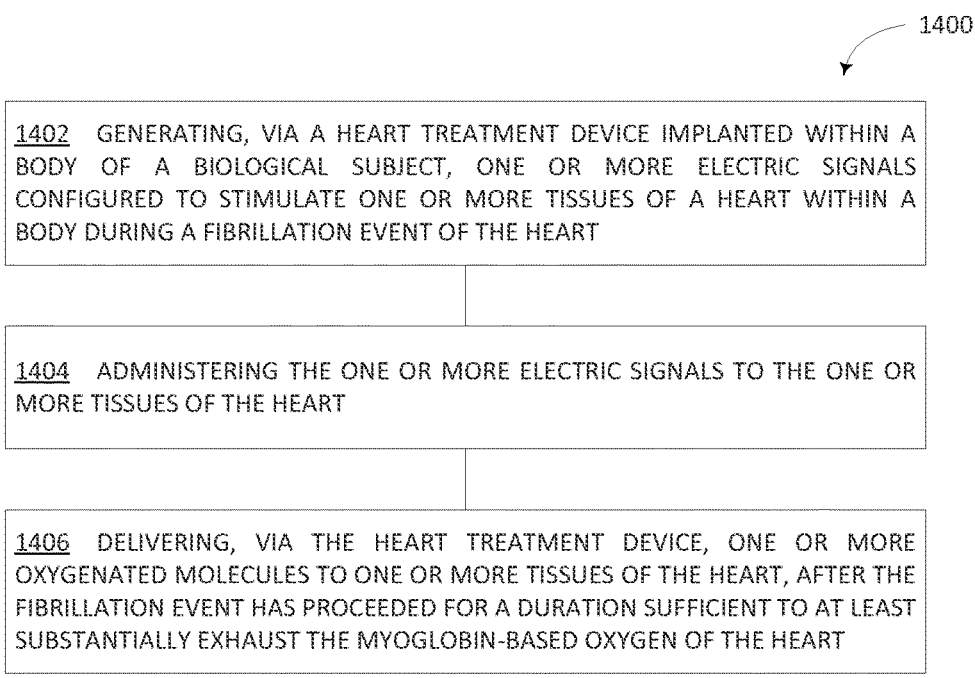
FIG. 14 is a flowchart of a method of treating a heart with an implanted heart treatment device.

FIG. 14 illustrates a method 1400 for treating a heart with an implanted heart treatment device in accordance with example embodiments. Method 1400 shows generating, via a heart treatment device implanted within a body of a biological subject, one or more electric signals configured to stimulate one or more tissues of a heart within a body during a fibrillation event of the heart in block 1402. For example, the electromagnetic generator 104 of system 100 can generate one or more electric signals configured to stimulate one or more tissues of a heart within a body during a fibrillation event of the heart, such as responsive to control by control circuitry 600. Method 1400 also includes administering the one or more electric signals to the one or more tissues of the heart in block 1404. For example, the electromagnetic generator 104 of system 100 can administer the one or more electric signals to the one or more tissues of the heart, such as responsive to control by control circuitry 600. Method 1400 also includes delivering, via the heart treatment device, one or more oxygenated molecules to one or more tissues of the heart, after the fibrillation event has proceeded for a duration sufficient to at least substantially exhaust the myoglobin-based oxygen of the heart in block 1406. For example, the oxygenator 106 can deliver one or more oxygenated molecules to blood via the oxygen exchange portion 202, when physiological sensors provide an indication of an occurrence and duration of a fibrillation event of the heart.

Figure 15:
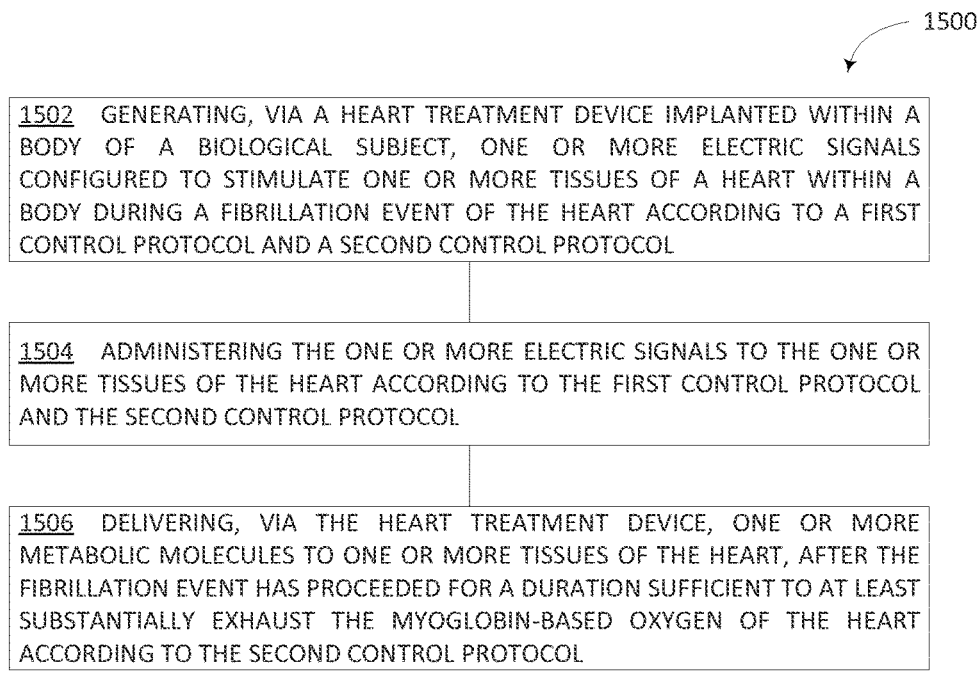
FIG. 15 is a flowchart of a method of treating a heart with an implanted heart treatment device.

FIG. 15 illustrates a method 1500 for treating a heart with an implanted heart treatment device in accordance with example embodiments. Method 1500 shows generating, via a heart treatment device implanted within a body of a biological subject, one or more electric signals configured to stimulate one or more tissues of a heart within a body during a fibrillation event of the heart according to a first control protocol and a second control protocol in block 1502. For example, the electromagnetic generator 704 of system 700 can generate one or more electric signals configured to stimulate one or more tissues of a heart within a body during a fibrillation event of the heart, responsive to control by control circuitry 708 upon execution of the first control protocol 710 and the second control protocol 712. Method 1500 also includes administering the one or more electric signals to the one or more tissues of the heart according to the first control protocol and the second control protocol in block 1504. For example, the electromagnetic generator 704 of system 700 can administer the one or more electric signals to the one or more tissues of the heart, responsive to control by control circuitry 708 upon execution of the first control protocol 710 and the second control protocol 712. Method 1500 also includes delivering, via the heart treatment device, one or more metabolic molecules to one or more tissues of the heart, after the fibrillation event has proceeded for a duration sufficient to at least substantially exhaust the myoglobin-based oxygen of the heart according to the second control protocol in block 1506. For example, the metabolic molecule delivery device 706 can deliver one or more metabolic molecules to blood, responsive to control by control circuitry 708 upon execution of the second control protocol 712.

Figure 16:
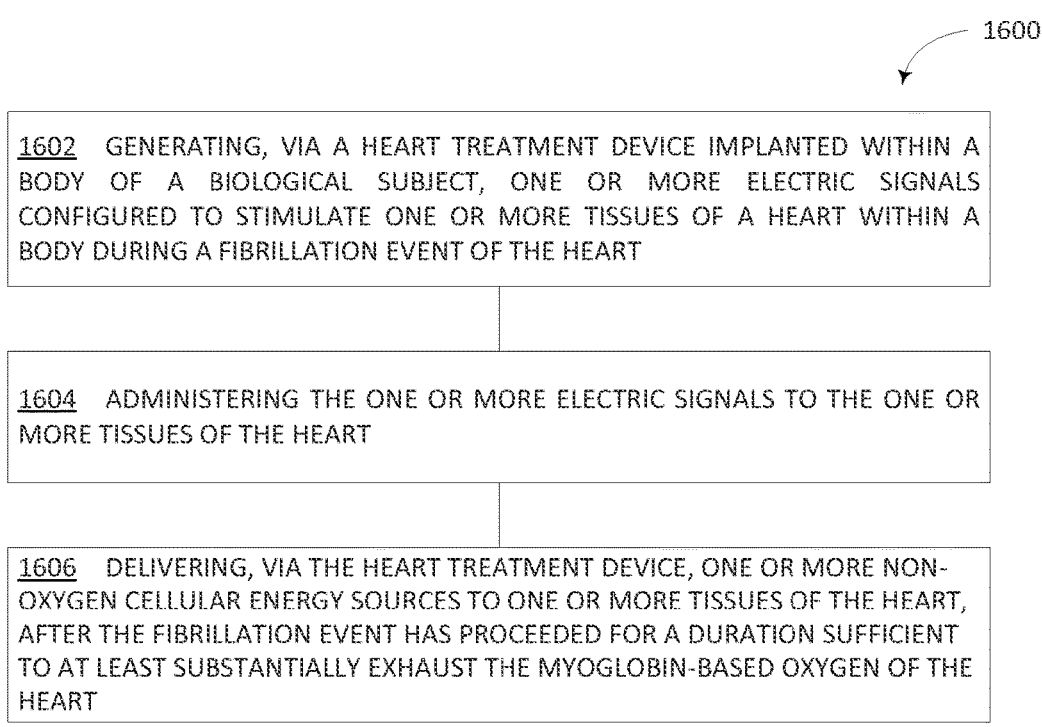
FIG. 16 is a flowchart of a method of treating a heart with an implanted heart treatment device.

FIG. 16 illustrates a method 1600 for treating a heart with an implanted heart treatment device in accordance with example embodiments. Method 1600 shows generating, via a heart treatment device implanted within a body of a biological subject, one or more electric signals configured to stimulate one or more tissues of a heart within a body during a fibrillation event of the heart in block 1602. For example, the electromagnetic generator 1104 of system 1100 can generate one or more electric signals configured to stimulate one or more tissues of a heart within a body during a fibrillation event of the heart, such as responsive to control by control circuitry 1200. Method 1600 also includes administering the one or more electric signals to the one or more tissues of the heart in block 1604. For example, the electromagnetic generator 1104 of system 1100 can administer the one or more electric signals to the one or more tissues of the heart, such as responsive to control by control circuitry 1200. Method 1600 also includes delivering, via the heart treatment device, one or more non-oxygen cellular energy sources to one or more tissues of the heart, after the fibrillation event has proceeded for a duration sufficient to at least substantially exhaust the myoglobin-based oxygen of the heart in block 1606. For example, the energy-carrier molecule delivery portion 1106 can deliver one or more non-oxygen cellular energy sources to blood via the energy molecule exchange portion 1112, when physiological sensors provide an indication of an occurrence and duration of a fibrillation event of the heart.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

At least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

At least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, based upon the teachings herein, changes and modifications can be made without departing from the subject matter described herein and its broader aspects and, therefore, the appended claims are to encompass within their scope all such changes and modifications as are within the true spirit and scope of the subject matter described herein.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An implantable heart treatment device, comprising:
   a substrate configured for implantation within a body;
   an electromagnetic signal generator coupled to the substrate and configured to generate one or more electric signals configured to stimulate one or more tissues of a heart within the body;
   an oxygenator coupled to the substrate and configured to supply one or more oxygenated molecules to one or more tissues of the heart within the body, the oxygenator including a blood inlet portion, a blood outlet portion, and an oxygen exchange portion positioned between the blood inlet portion and the blood outlet portion, the oxygen exchange portion including a high surface area oxygen exchanger configured to transfer one or more oxygenated molecules from the high surface area oxygen exchanger to blood passing from the blood inlet portion to the blood outlet portion; and control circuitry configured to generate one or more control signals to activate one or more of the electromagnetic signal generator and the oxygenator during a fibrillation event of the heart.

2. The implantable heart treatment device of claim 1, wherein the oxygenator includes a reservoir configured to store the one or more oxygenated molecules.

3. The implantable heart treatment device of claim 1, further comprising:
a reservoir coupled to the substrate, in fluid communication with the oxygenator, and configured to store the one or more oxygenated molecules.

4. The implantable heart treatment device of claim 1, wherein the one or more oxygenated molecules are stored on the high surface area oxygen exchanger via adsorption.

5. The implantable heart treatment device of claim 1, wherein the one or more oxygenated molecules are positioned within one or more carrier molecules.

6. The implantable heart treatment device of claim 5, wherein the one or more carrier molecules include at least one of one or more liposomes, one or more micelles, or one or more perflurocarbons.

7. The implantable heart treatment device of claim 1, wherein the high surface area oxygen exchanger includes a surface area configured for the exchange of the one or more oxygenated molecules of between approximately 0.001 square meters and approximately 5 square meters.

8. The implantable heart treatment device of claim 1, wherein the high surface area oxygen exchanger includes one or more hollow fibers through which one of blood and the oxygenated molecules is configured to pass, with an exterior surface of the one or more hollow fibers configured to contact the corresponding other of blood and the oxygenated molecules.

9. The implantable heart treatment device of claim 8, wherein the one or more hollow fibers are constructed from one or more of silicone, polypropylene, and polymethylpentene.

10. The implantable heart treatment device of claim 1, wherein at least one of the blood inlet portion and the blood outlet portion includes at least one conduit having an internal diameter of greater than ten microns.

11. The implantable heart treatment device of claim 1, wherein the blood inlet portion includes one or more ports configured to receive blood from at least one vein of the body.

12. The implantable heart treatment device of claim 11, wherein the blood inlet portion includes one or more ports configured to receive blood from at least one of one or more cardiac veins of the heart, a superior vena cava (SVC), or an inferior vena cava (IVC).

13. The implantable heart treatment device of claim 1, wherein the blood inlet portion includes one or more ports configured to receive blood from at least one artery of the body.

14. The implantable heart treatment device of claim 1, wherein the blood outlet portion includes one or more ports configured to return blood from the oxygen exchange portion to at least one vein of the body.

15. The implantable heart treatment device of claim 1, wherein the blood outlet portion includes one or more ports configured to return blood from the oxygen exchange portion to a position directly within the heart.

16. The implantable heart treatment device of claim 1, wherein the blood outlet portion includes one or more ports configured to return blood from the oxygen exchange portion to at least one artery of the body.

17. The implantable heart treatment device of claim 16, wherein the blood outlet portion includes one or more ports configured to return blood from the oxygen exchange portion to at least one of at least one coronary artery of the heart, the ascending aorta, the descending aorta, or the aortic arch.

18. The implantable heart treatment device of claim 1, wherein the control circuitry is configured to receive one or more sense signals from one or more physiological sensors configured to measure one or more physiological parameters representative of the condition of the heart.

19. The implantable heart treatment device of claim 1, wherein the oxygenator is configured to supply one or more materials in addition to the one or more oxygenated molecules.

20. The implantable heart treatment device of claim 19, wherein the one or more materials in addition to the one or more oxygenated molecules include at least one of hydrogen sulfide, carbon dioxide, carbon monoxide, nitric oxide, nitrous oxide, nitrogen dioxide, and iodide and salts thereof.

21. The implantable heart treatment device of claim 1, wherein the oxygenator includes at least one of a chemical reactor configured to generate the one or more oxygenated molecules as a product of a chemical reaction within the chemical reactor or an electrochemical reactor configured to generate the one or more oxygenated molecules as a product of an electrochemical reaction within the electrochemical reactor.

22. The implantable heart treatment device of claim 1, further comprising at least one of a chemical reactor coupled to the substrate, in fluid communication with the oxygenator, and configured to generate the one or more oxygenated molecules as a product of a chemical reaction within the chemical reactor or an electrochemical reactor coupled to the substrate, in fluid communication with the oxygenator, and configured to generate the one or more oxygenated molecules as a product of an electrochemical reaction within the electrochemical reactor.

23. The implantable heart treatment device of claim 1, wherein the oxygenator includes at least one of a blood pump or a controllable valve.

24. An implantable heart treatment device, comprising:
a substrate configured for implantation within a body;
an electromagnetic signal generator coupled to the substrate and configured to generate one or more electric signals configured to stimulate one or more tissues of a heart within the body;
an oxygenator coupled to the substrate and configured to supply one or more oxygenated molecules to one or more tissues of the heart within the body, the oxygenator including a blood inlet portion, a blood outlet portion, and an oxygen exchange portion positioned between the blood inlet portion and the blood outlet portion, the oxygen exchange portion including a high surface area oxygen exchanger configured to transfer one or more oxygenated molecules from the high surface area oxygen exchanger to blood passing from the blood inlet portion to the blood outlet portion; and
control circuitry configured to generate one or more control signals to activate one or more of the electromagnetic signal generator and the oxygenator, wherein the control circuitry is configured to receive one or more sense signals from one or more physiological sensors configured to measure one or more physiological parameters representative of the condition of the heart, and wherein the control circuitry is configured to make a determination pertaining to a fibrillation event of the heart based on the one or more sense signals received from the one or more physiological sensors.

25. The implantable heart treatment device of claim 24, wherein the control circuitry is configured to activate one or more of the electromagnetic signal generator and the oxygenator based on the determination pertaining to the fibrillation event of the heart.

26. An implantable heart treatment device, comprising:
a substrate configured for implantation within a body;
an electromagnetic signal generator coupled to the substrate and configured to generate one or more electric signals configured to stimulate one or more tissues of a heart within the body;
an oxygenator coupled to the substrate and configured to supply one or more oxygenated molecules to one or more tissues of the heart within the body, the oxygenator including a blood inlet portion, a blood outlet portion, and an oxygen exchange portion positioned between the blood inlet portion and the blood outlet portion, the oxygen exchange portion including a high surface area oxygen exchanger configured to transfer one or more oxygenated molecules from the high surface area oxygen exchanger to blood passing from the blood inlet portion to the blood outlet portion; and
control circuitry configured to generate one or more control signals to activate one or more of the electromagnetic signal generator and the oxygenator responsive to one or more commands from an external device.

* * * * *